Figure 1A:
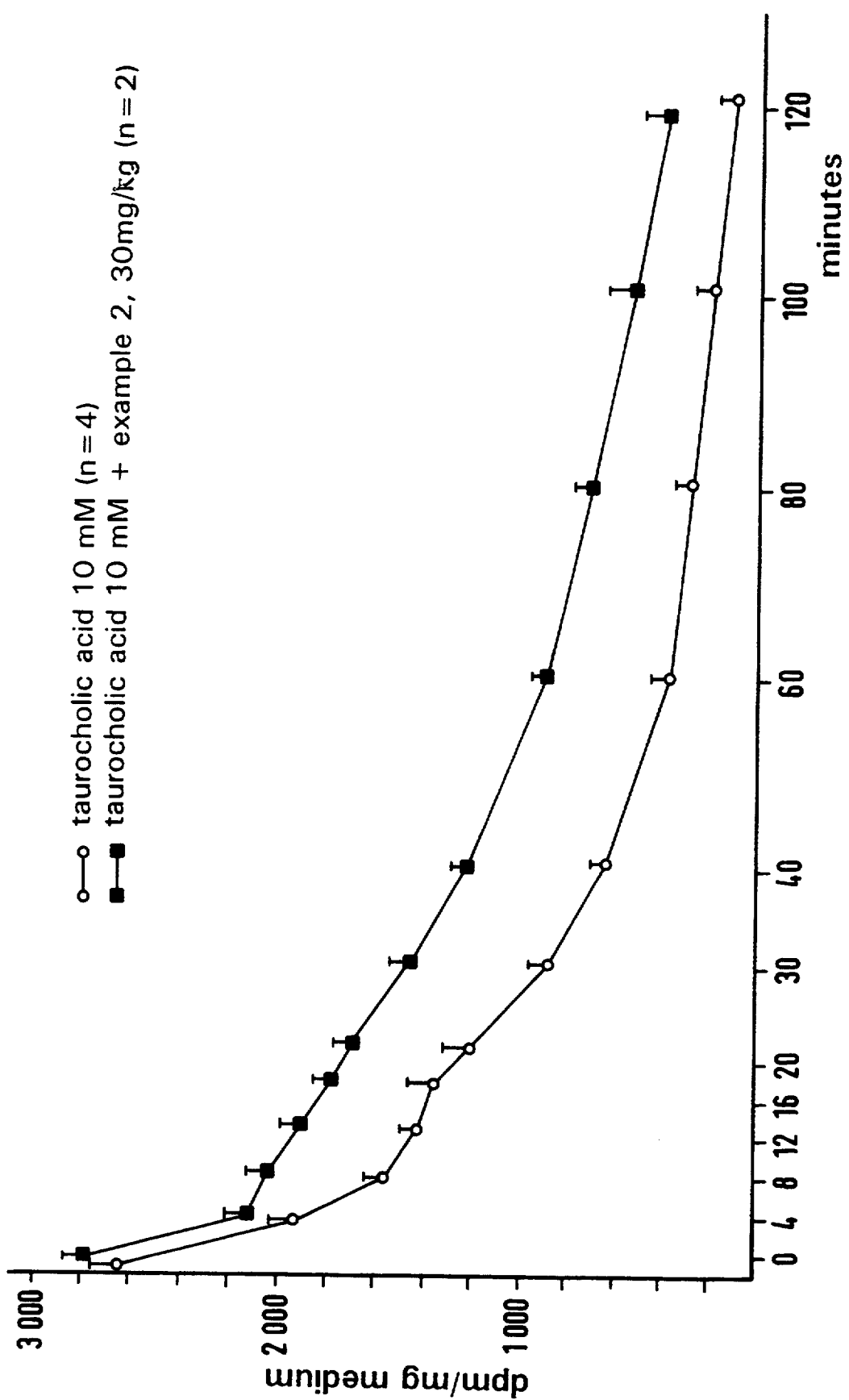
Figure 1B:
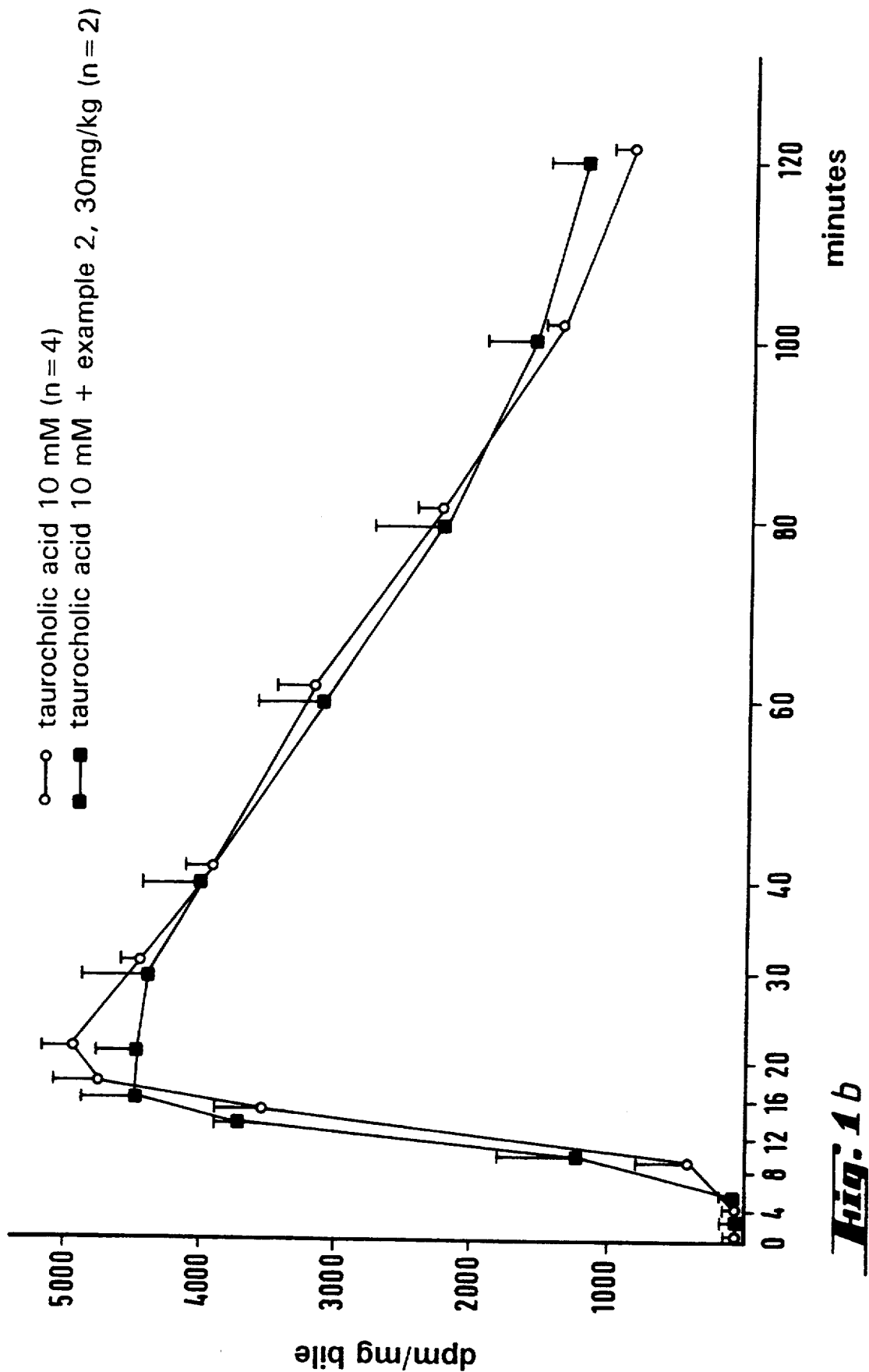
Figure 2A:
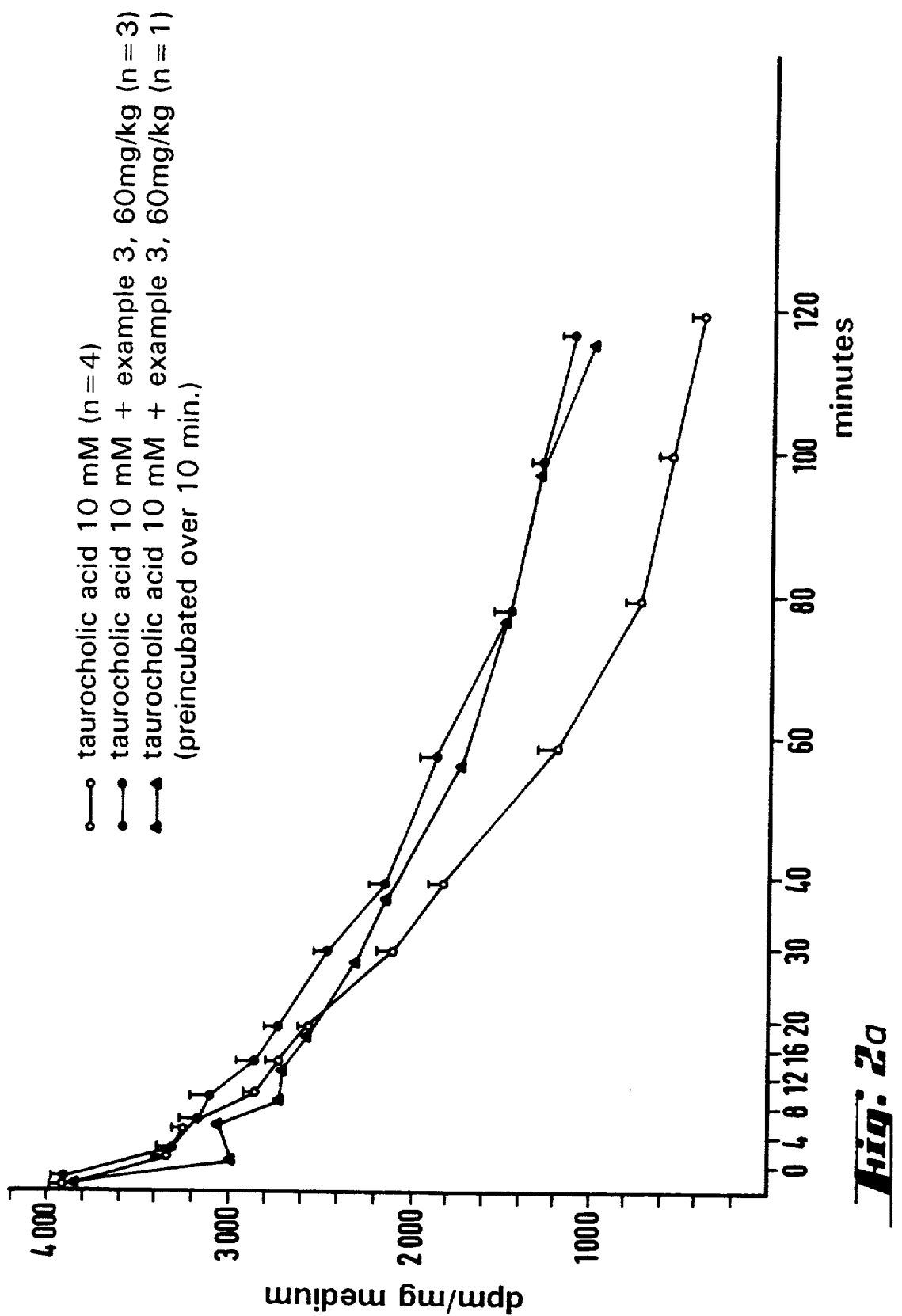
Figure 2B:
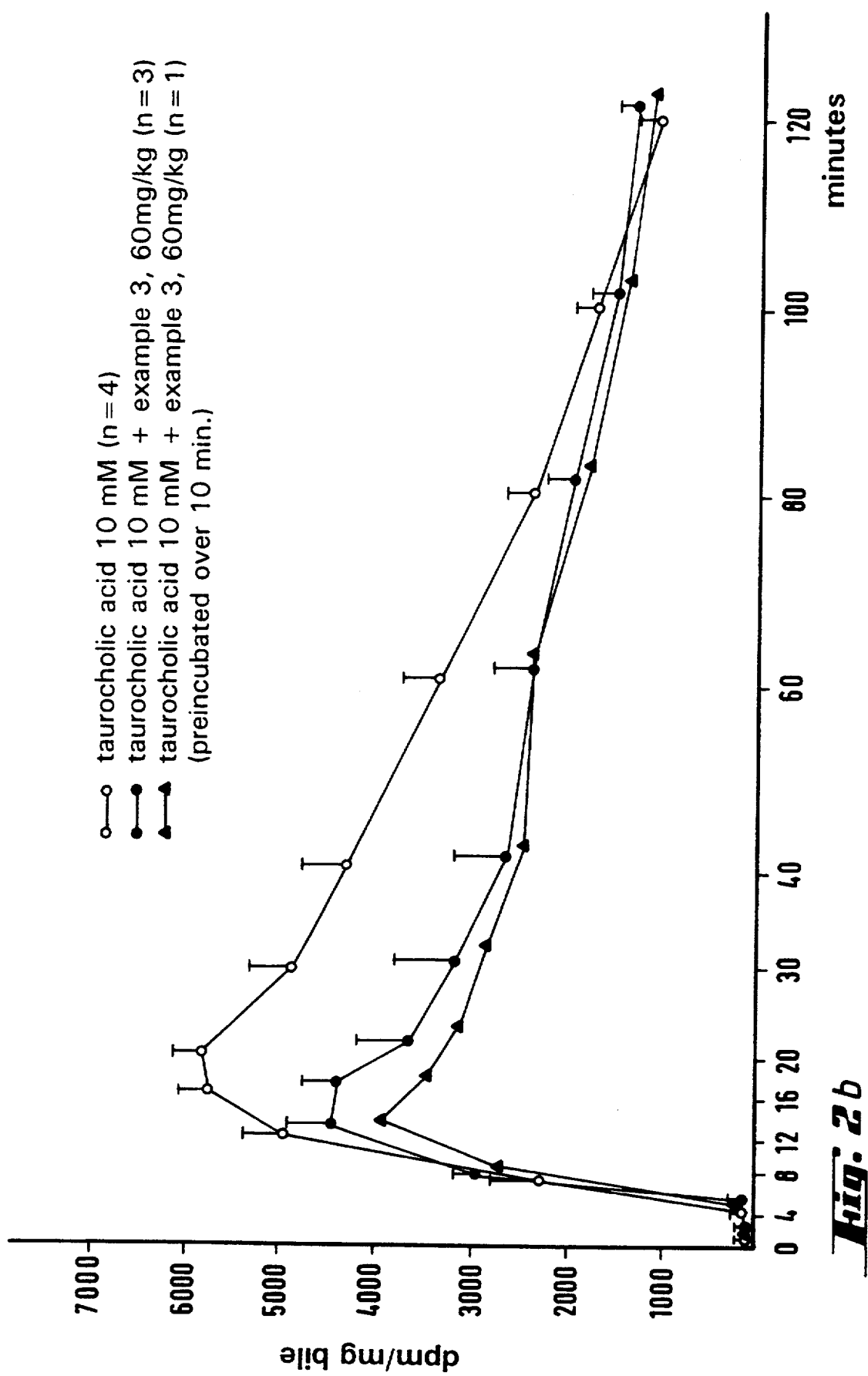
Figure 3A:
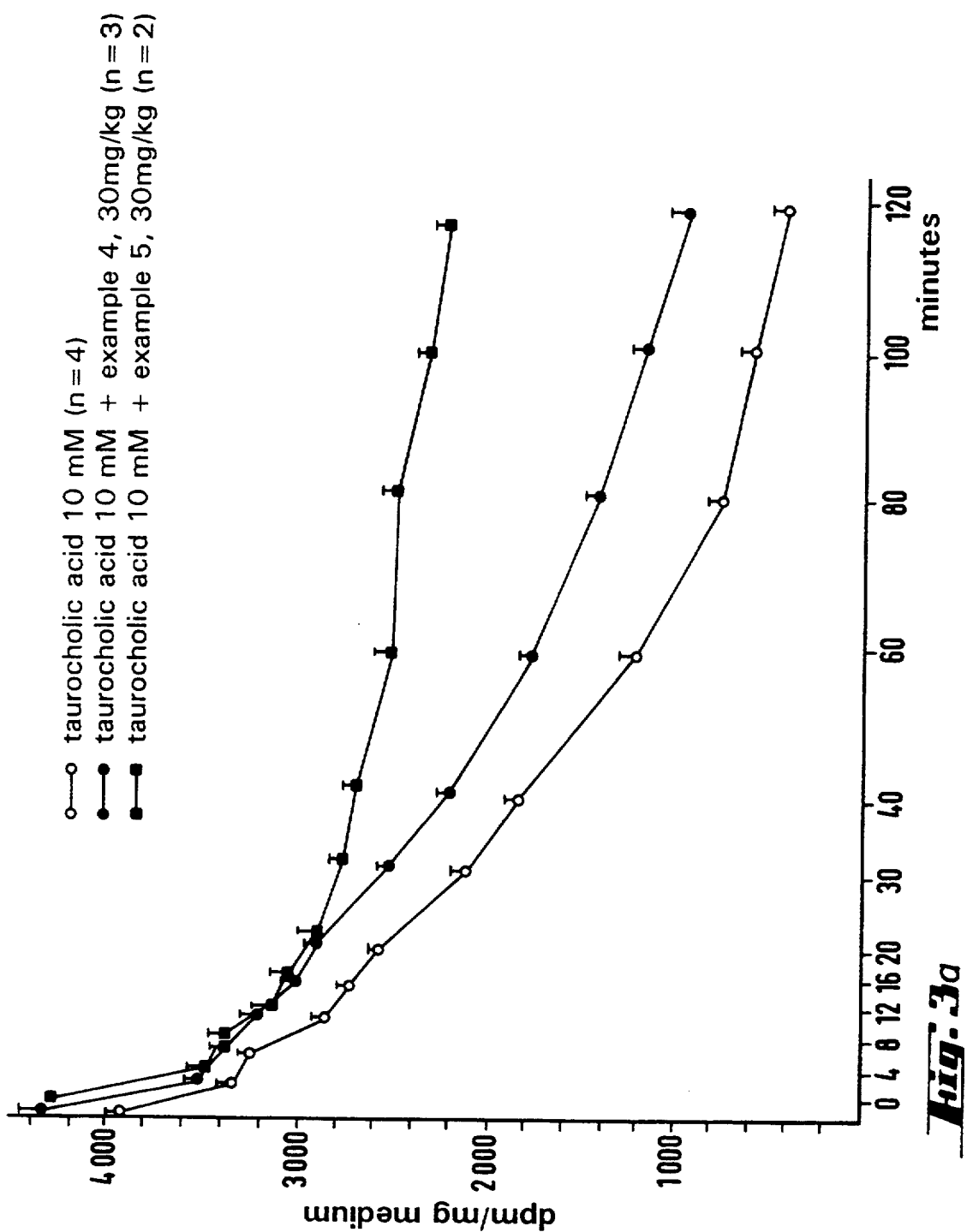
Figure 3B:
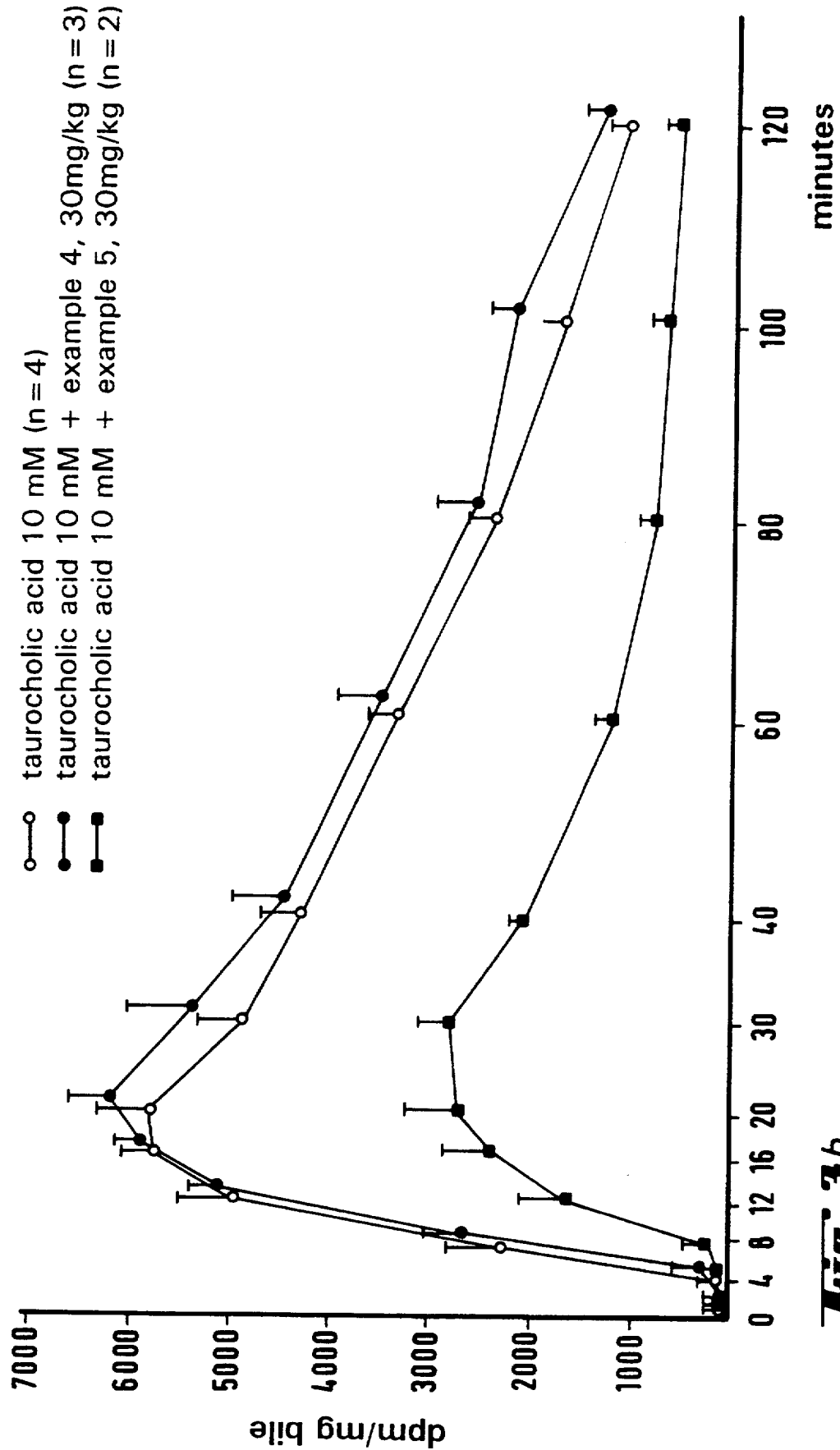
Figure 4A:
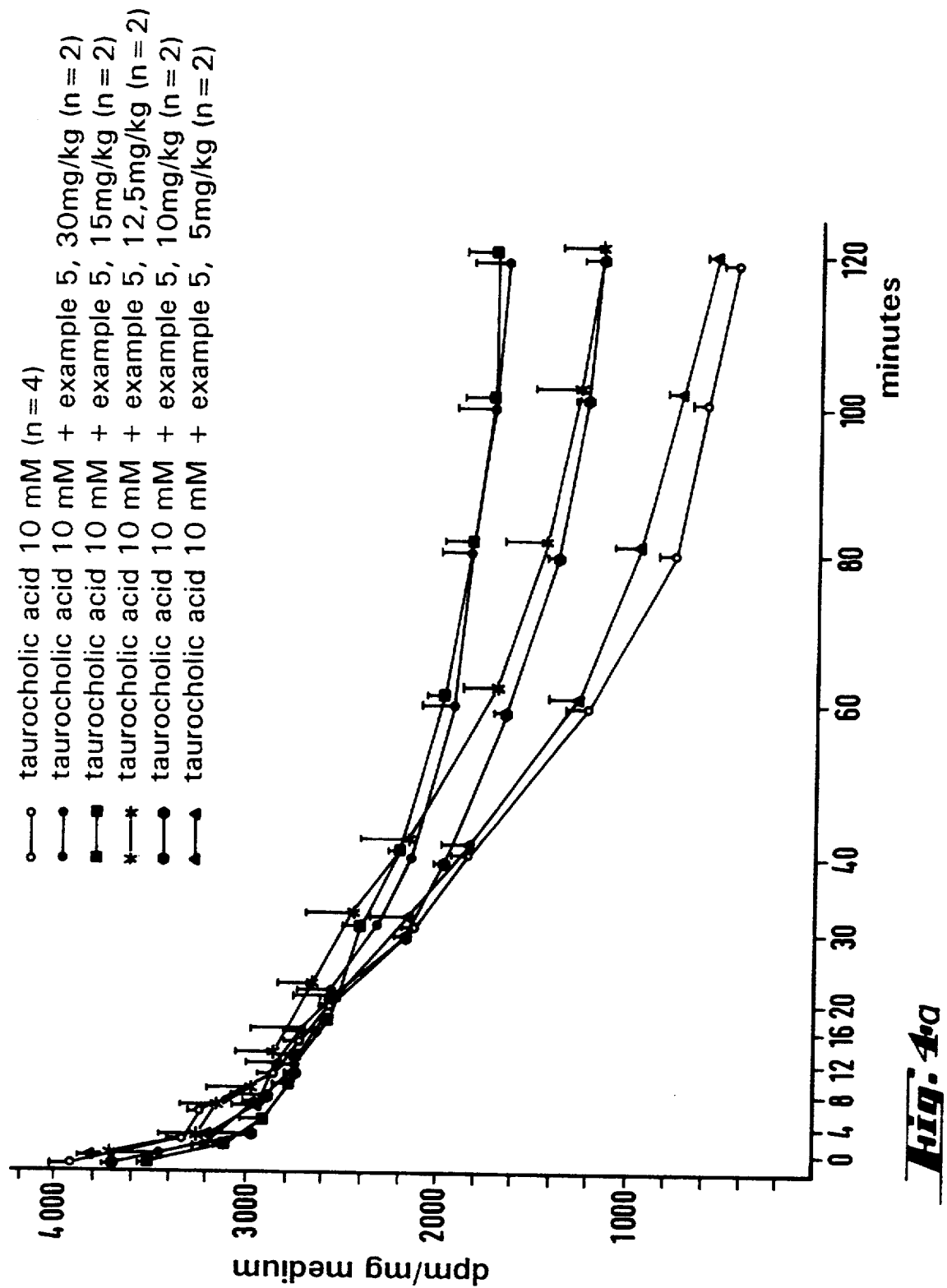
Figure 5B:
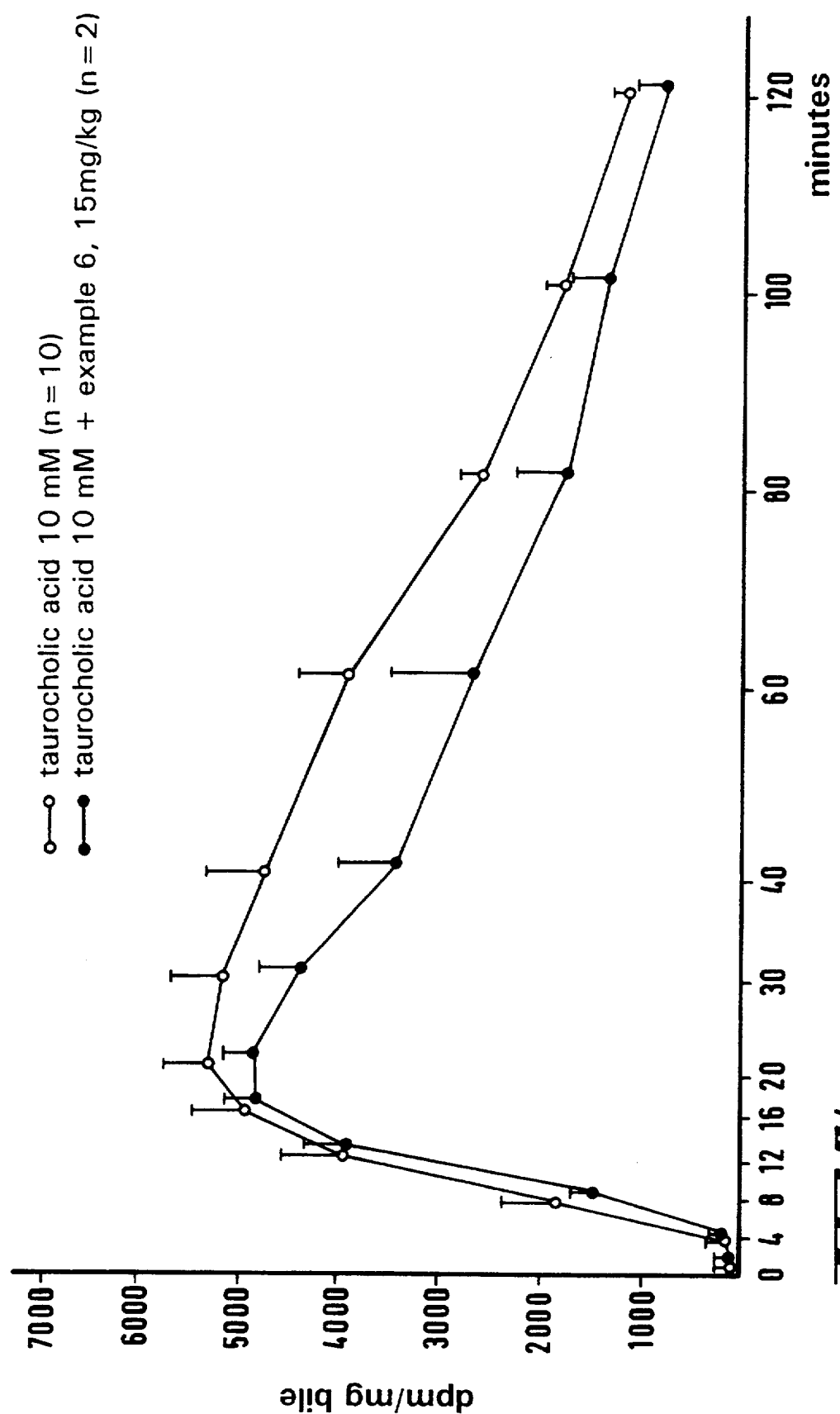
Figure 6A:
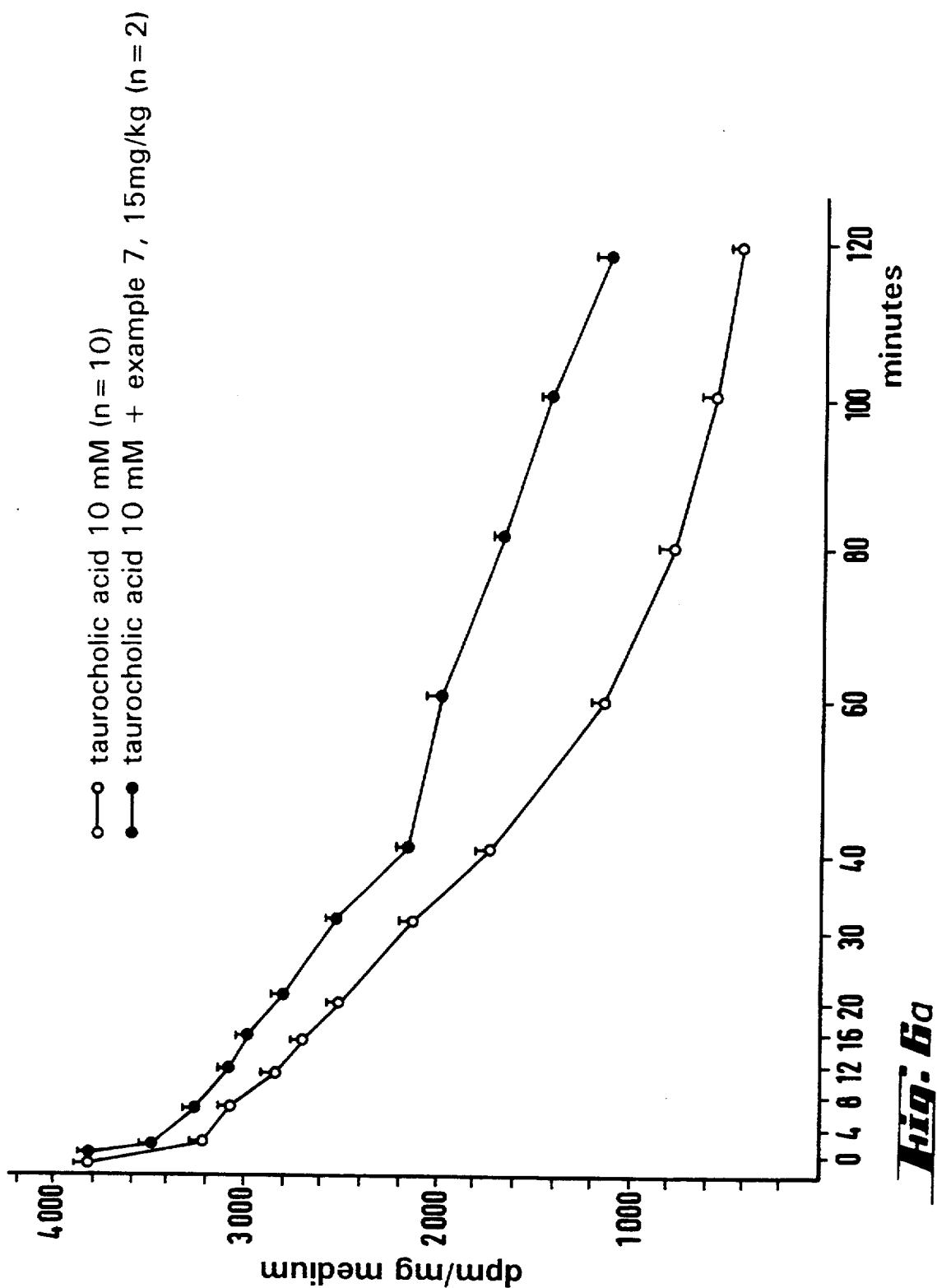
Figure 6B:
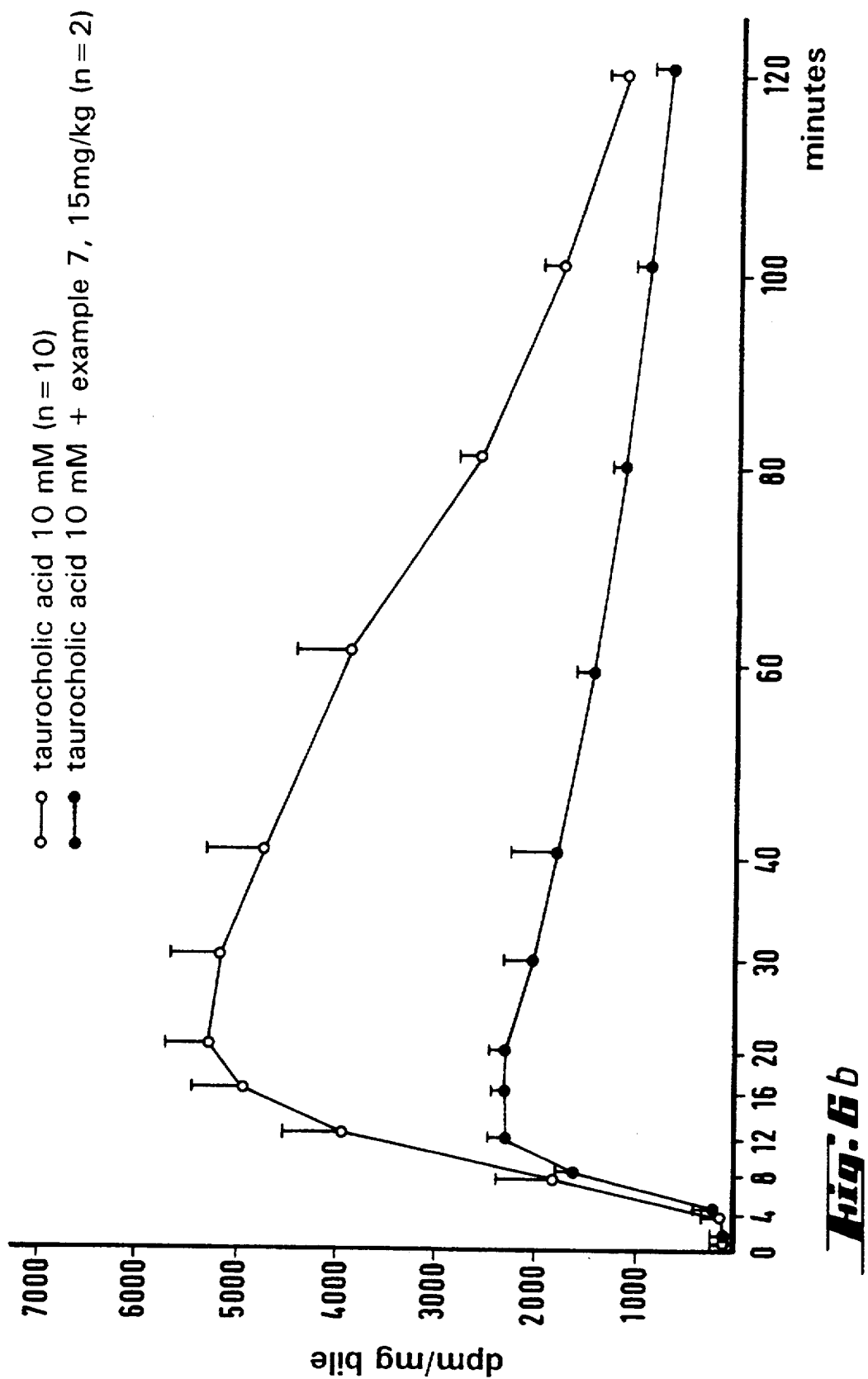
Figure 7A:
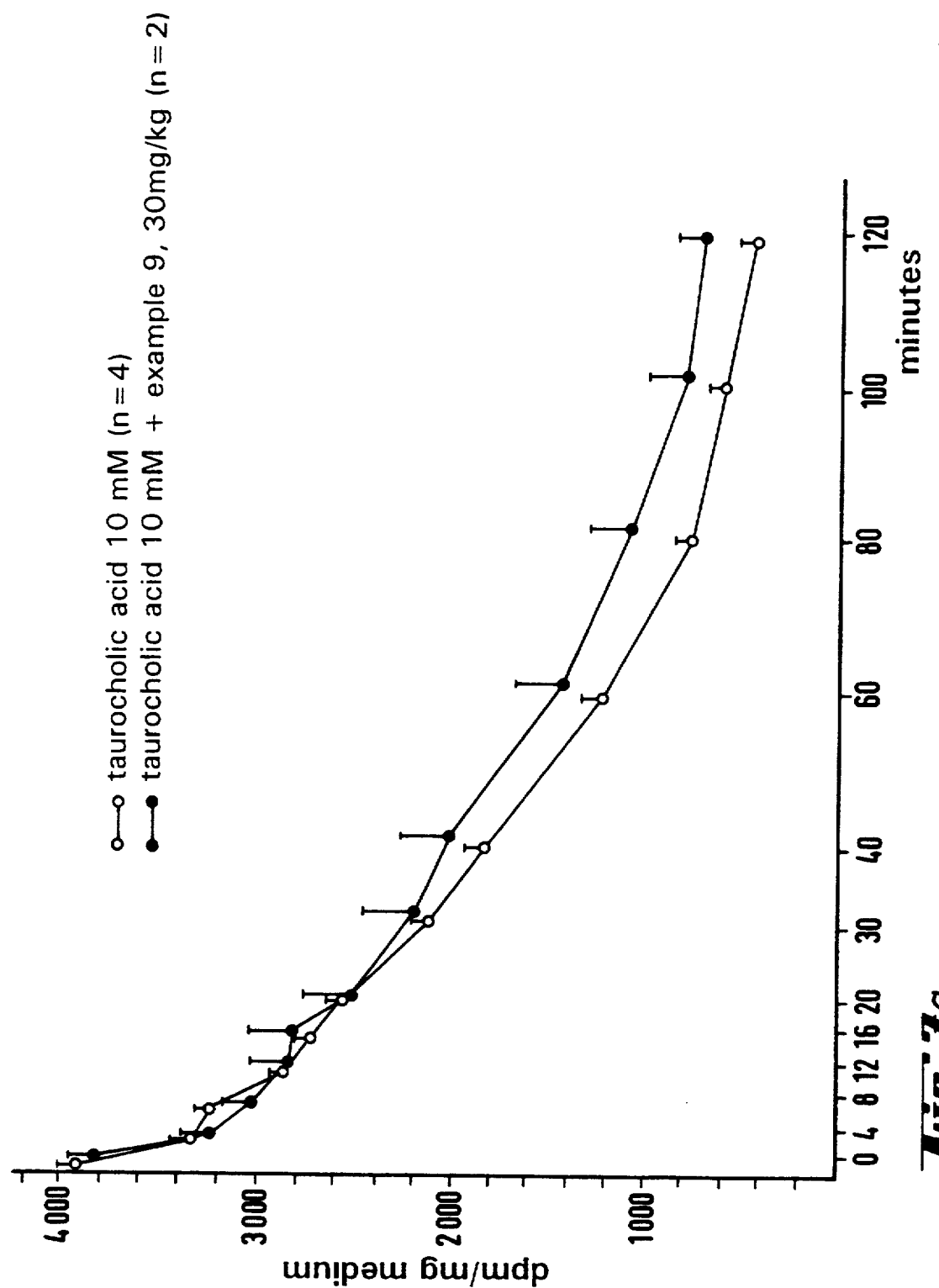
Figure 7B:
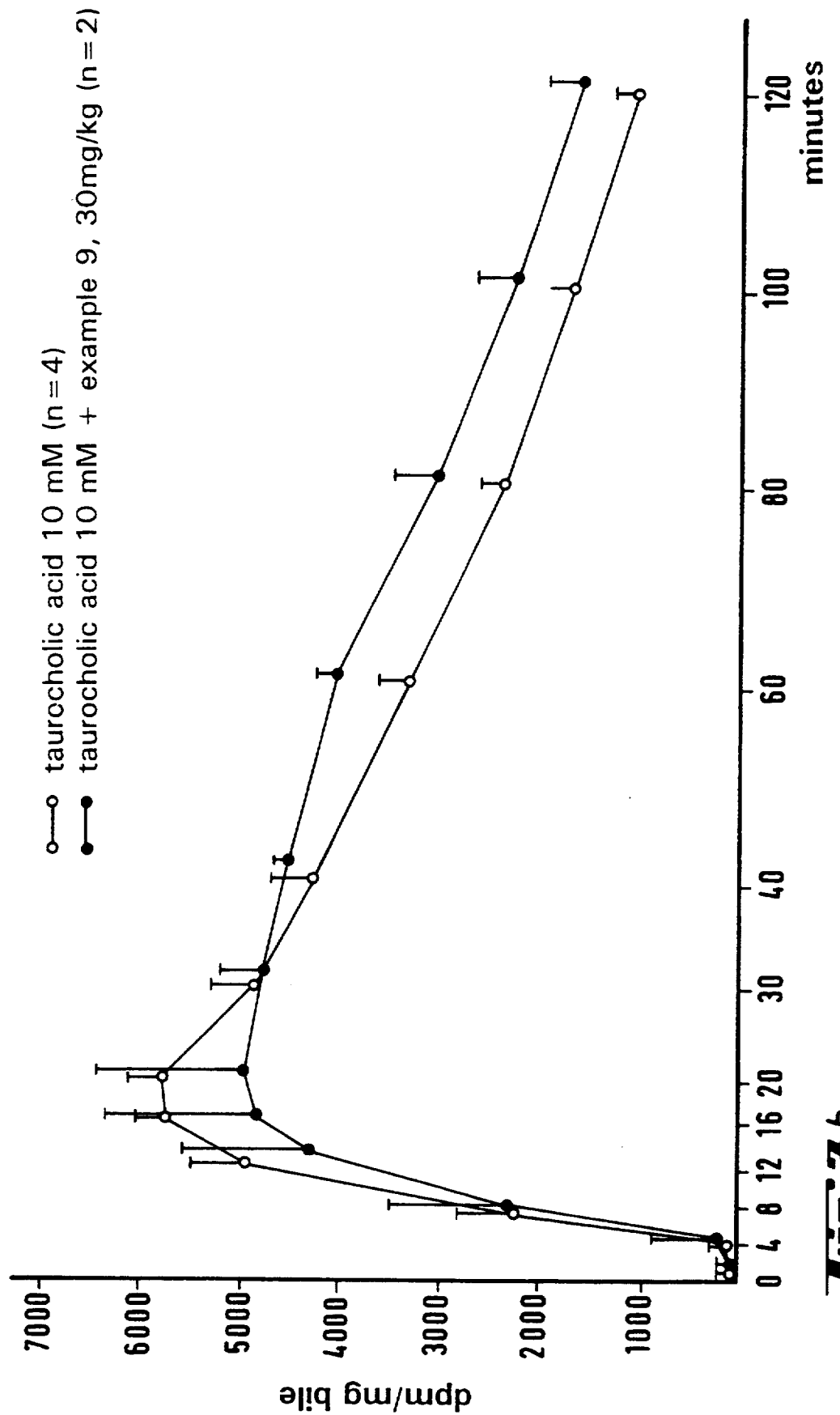
Figure 8A:
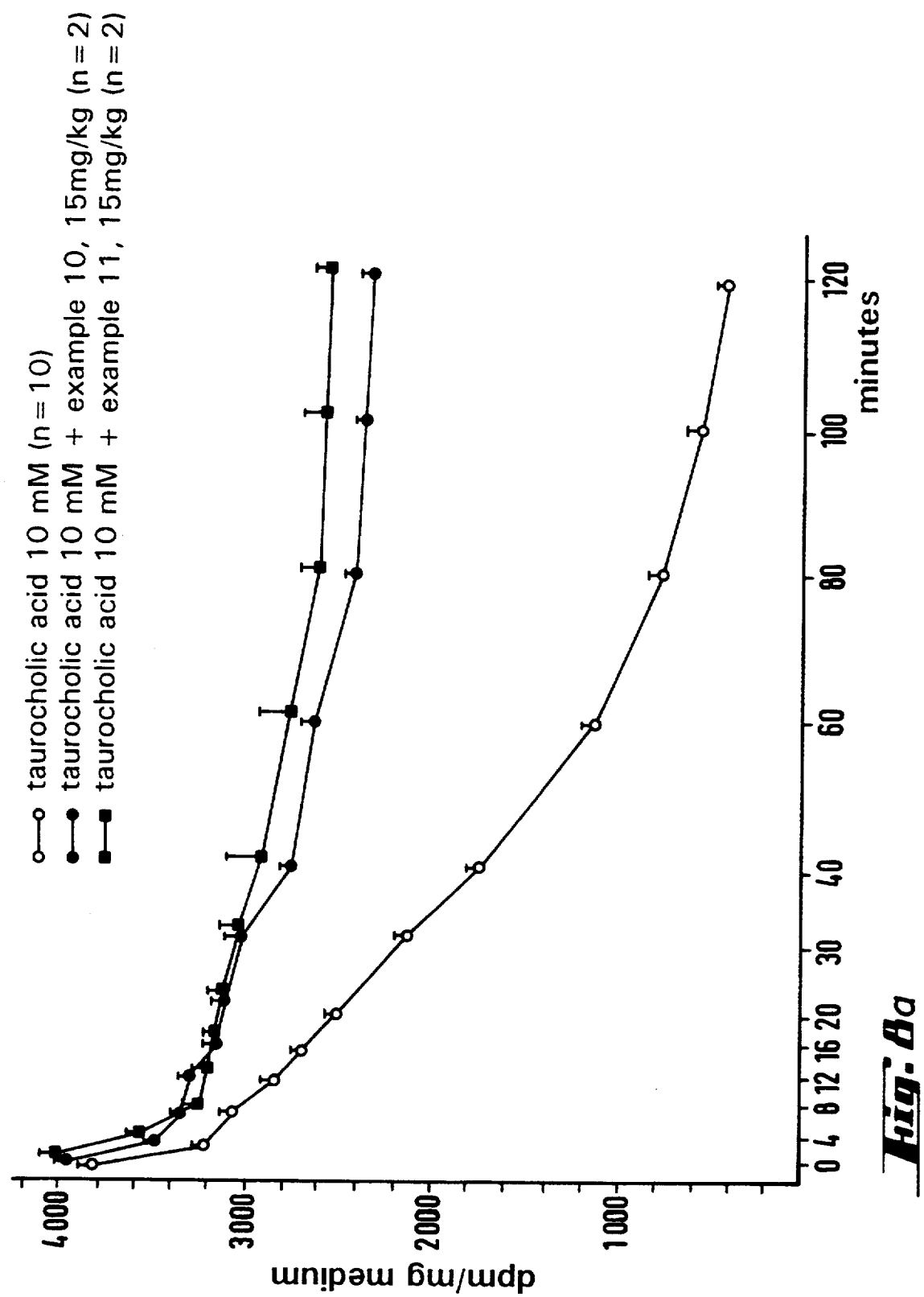
Figure 8B:
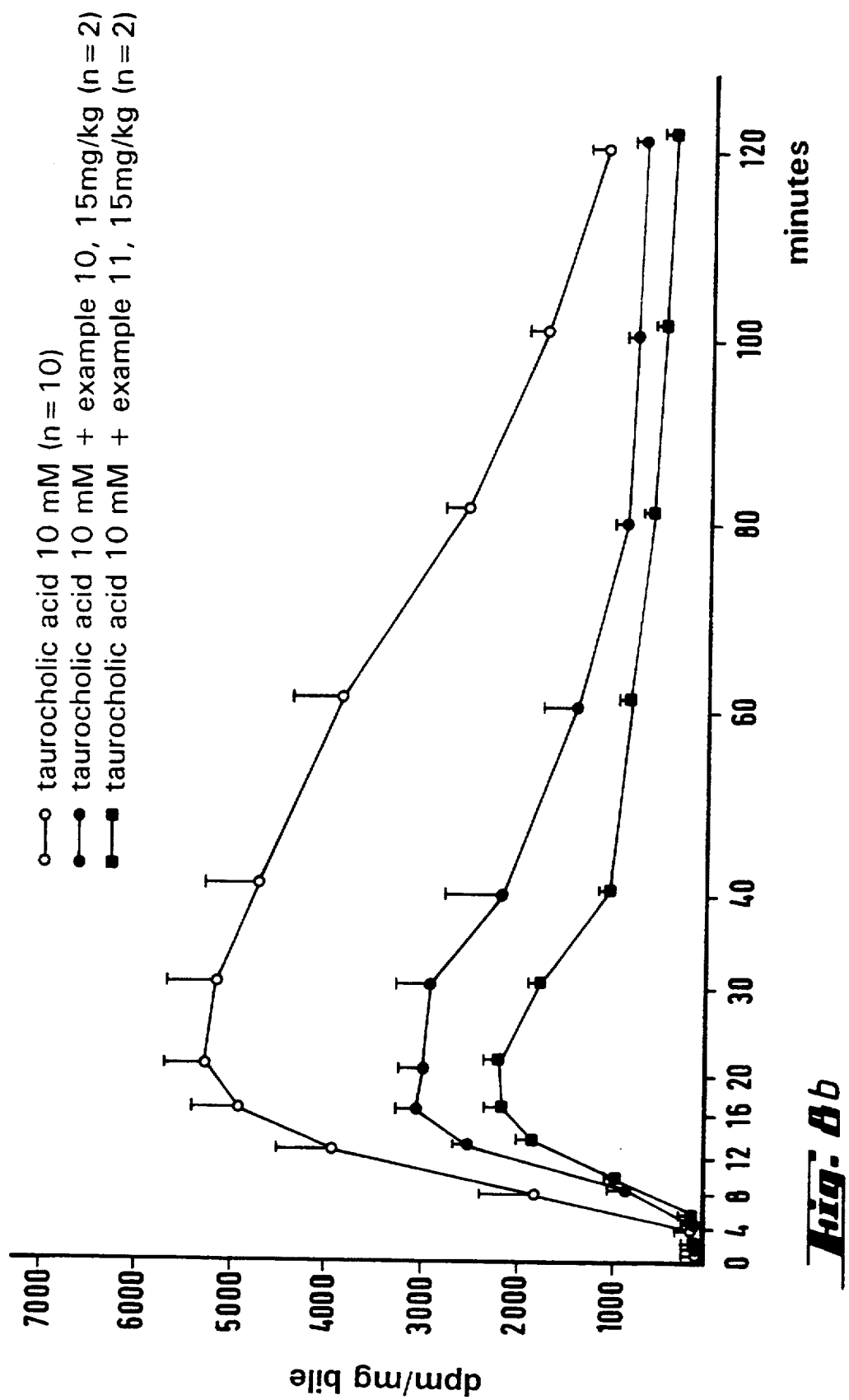
Figure 9B:
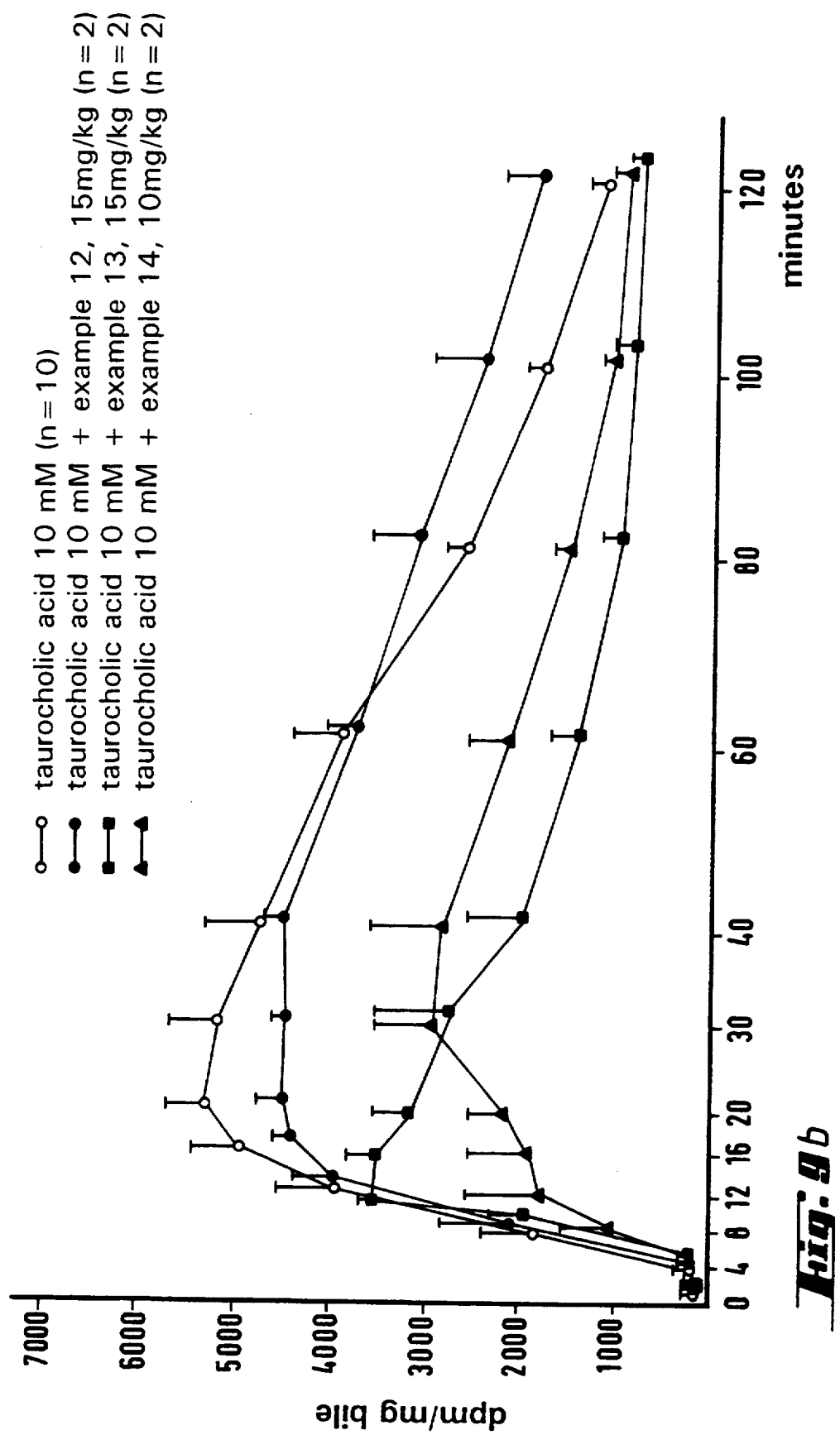
Figure 10A:
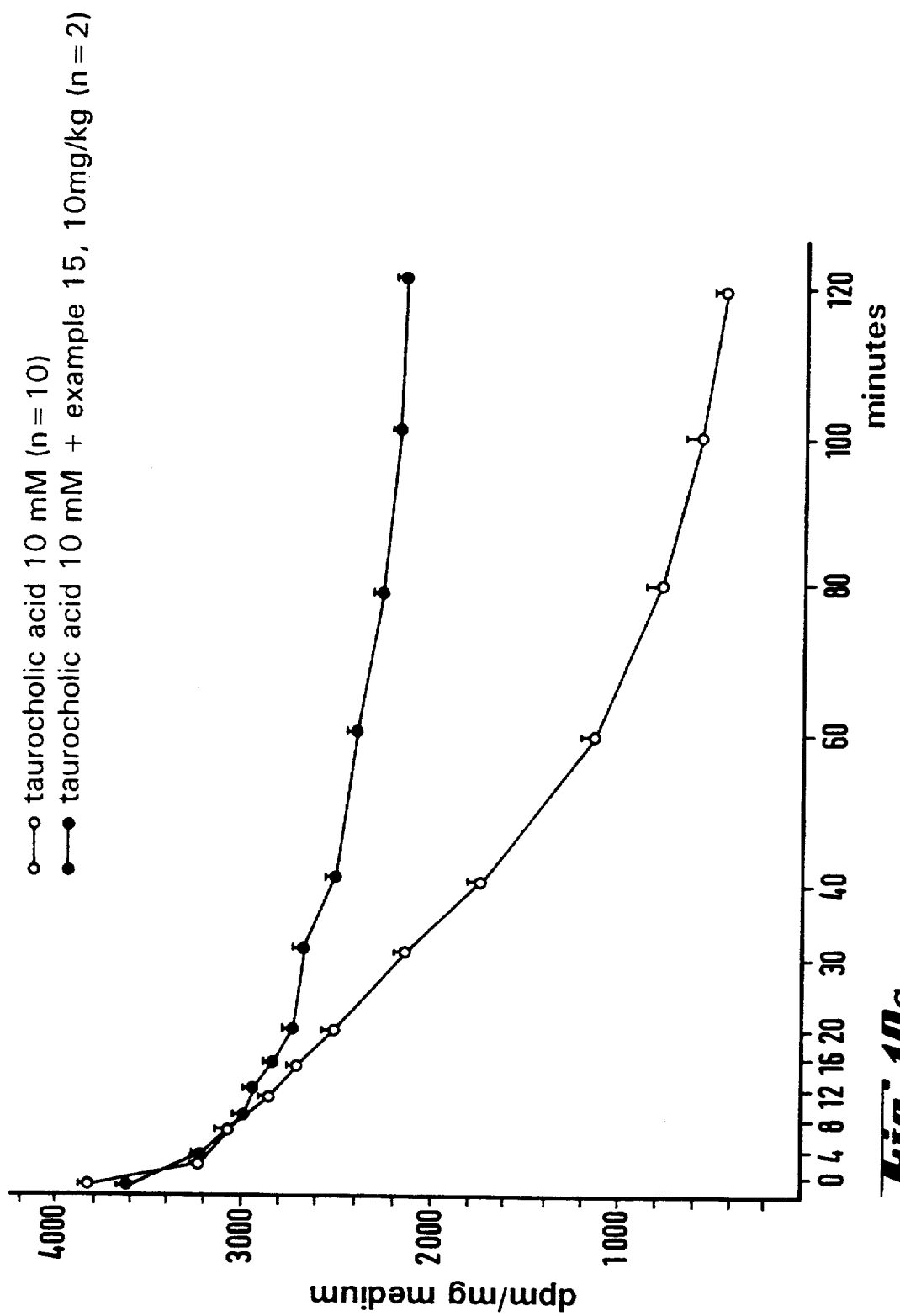

United States Patent [19]

Kramer et al.

[11] Patent Number: 5,430,116

[45] Date of Patent: Jul. 4, 1995

[54] POLYMERS AND OLIGOMERS OF BILE ACID DERIVATIVES, PROCESS FOR THEIR PREPARATION AND THEIR USE AS PHARMACEUTICALS

[75] Inventors: Werner Kramer, Mainz; Stefan Müllner, Hochheim am Main; Matthias Gutweiler, Taunusstein; Matthias Kroggel, Kelkheim, all of Germany

[73] Assignee: Hoechst Aktiengesellschaft, Frankfurt am Main, Germany

[21] Appl. No.: 992,411

[22] Filed: Dec. 17, 1992

[30] Foreign Application Priority Data

Dec. 20, 1991 [DE] Germany ............... 41 42 379.8

[51] Int. Cl.$^6$ ............... C08F 232/08; C08F 226/10; C08F 222/04; C08F 222/02; C08F 222/10
[52] U.S. Cl. ............... 526/284; 526/264; 526/240; 526/271; 526/286; 526/317.1; 526/328.5
[58] Field of Search ............ 526/284, 264, 271, 317.1, 526/328.5, 240

[56] References Cited

U.S. PATENT DOCUMENTS

| | | | |
|---|---|---|---|
| 3,383,281 | 5/1968 | Wolf et al. | 167/65 |
| 3,709,867 | 1/1973 | Karabinos et al. | 260/28.5 A |
| 4,104,285 | 8/1978 | Gallo-Torres et al. | 260/397.1 |

FOREIGN PATENT DOCUMENTS

| | | |
|---|---|---|
| 0417725 | 9/1990 | European Pat. Off. . |
| 0489423 | 12/1991 | European Pat. Off. . |
| 4142323.2 | 12/1992 | Germany . |
| 0525709 | 8/1976 | U.S.S.R. . |

OTHER PUBLICATIONS

CA 85: 193309u, 1976–an abstract of L.
Cayen, Pharmac. Ther. vol. 29, pp. 157-204, 1985.
Krause et al., Atherosclerosis VIII, G. Crepaldi et al., editors, Excerpta Medica, 1989, pp. 707-710.
Vaccaro et al., Atherosclerosis VIII, G. Crepaldi et al., editors, Excerpta Medica, 1989, pp. 605-608.
Reale, Attilio, Atherosclerosis VIII, G. Crepaldi et al., editors, Excerpta Medica, 1989, pp. 541-545.
Redel et al., Bulletin of the Chemical Society of France, pp. 877-883, 1949.
Jones et al., Journal of the Chemical Society, pp. 2164-2168, 1949.
Chemical Abstracts, vol. 85, No. 26, Dec. 27, 1976, No. 85:193309u.

*Primary Examiner*—Joseph L. Schofer
*Assistant Examiner*—Wu C. Cheng
*Attorney, Agent, or Firm*—Finnegan, Henderson, Farabow, Garrett & Dunner

[57] ABSTRACT

Polymeric and oligomeric bile acids are described which can be prepared by polymerization of monomeric bile acids of the formula I $$G-X-A \qquad (I)$$

in which G, X and A have the given meanings or by copolymerization with a monomer of the formula IV $$\overset{R^9}{\underset{|}{H_2C=C-R^{10}}} \qquad (IV)$$

in which $R^9$ and $R^{10}$ have the given meanings, or by copolymerization with N-vinylpyrrolidone or its derivatives, and/or by copolymerization with ethylenically unsaturated dicarboxylic anhydrides and ethylenically unsaturated dicarboxylic acids each having 2 to 6 carbon atoms; their esters or half esters, alkyl esters having 1-6 carbon atoms, cycloalkyl esters having 5 to 8 carbon atoms, benzyl esters or phenyl esters being understood as esters. They can be used as pharmaceuticals, foodstuff additives, formulation auxiliaries and detergents.

17 Claims, 22 Drawing Sheets

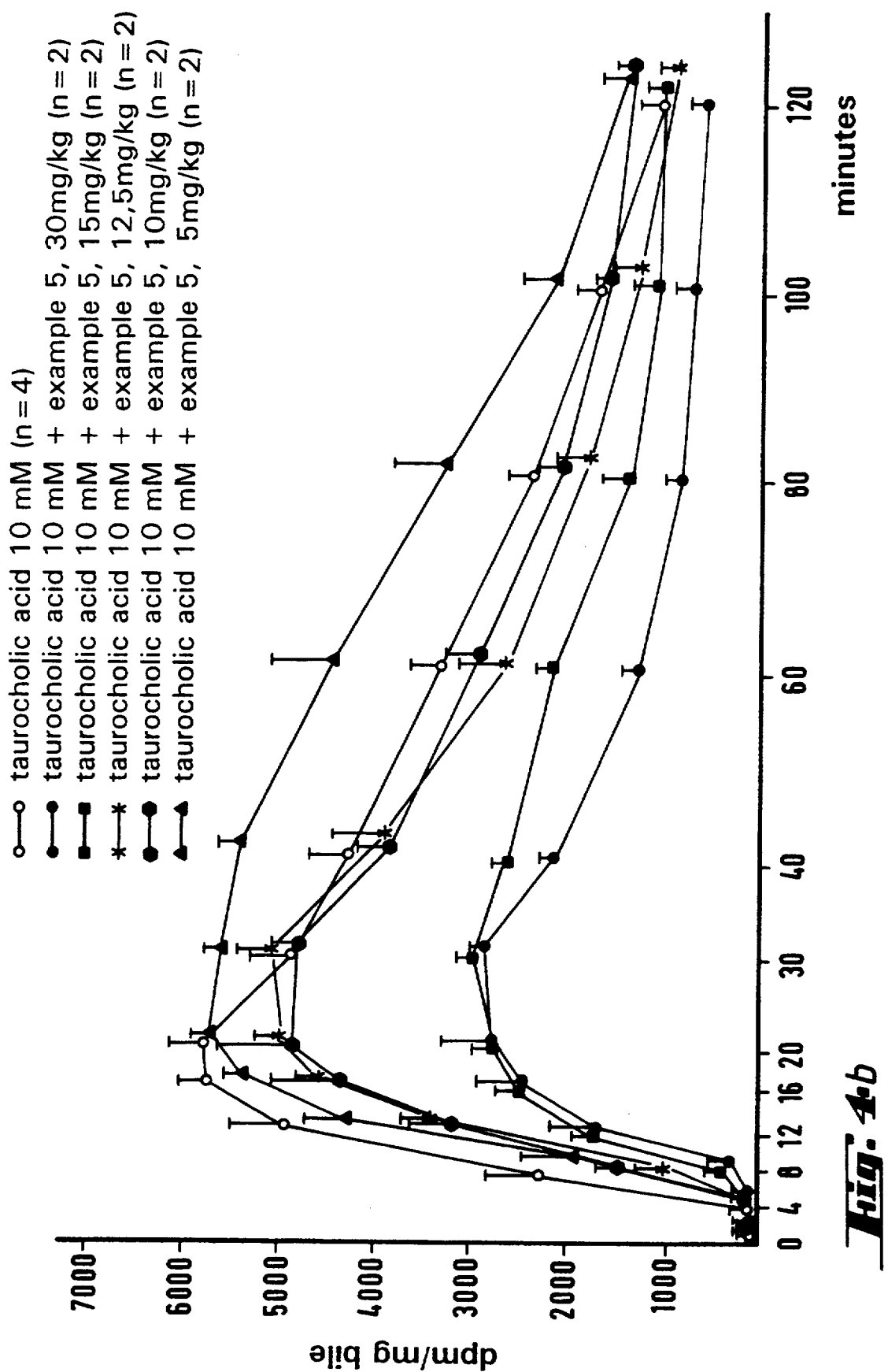

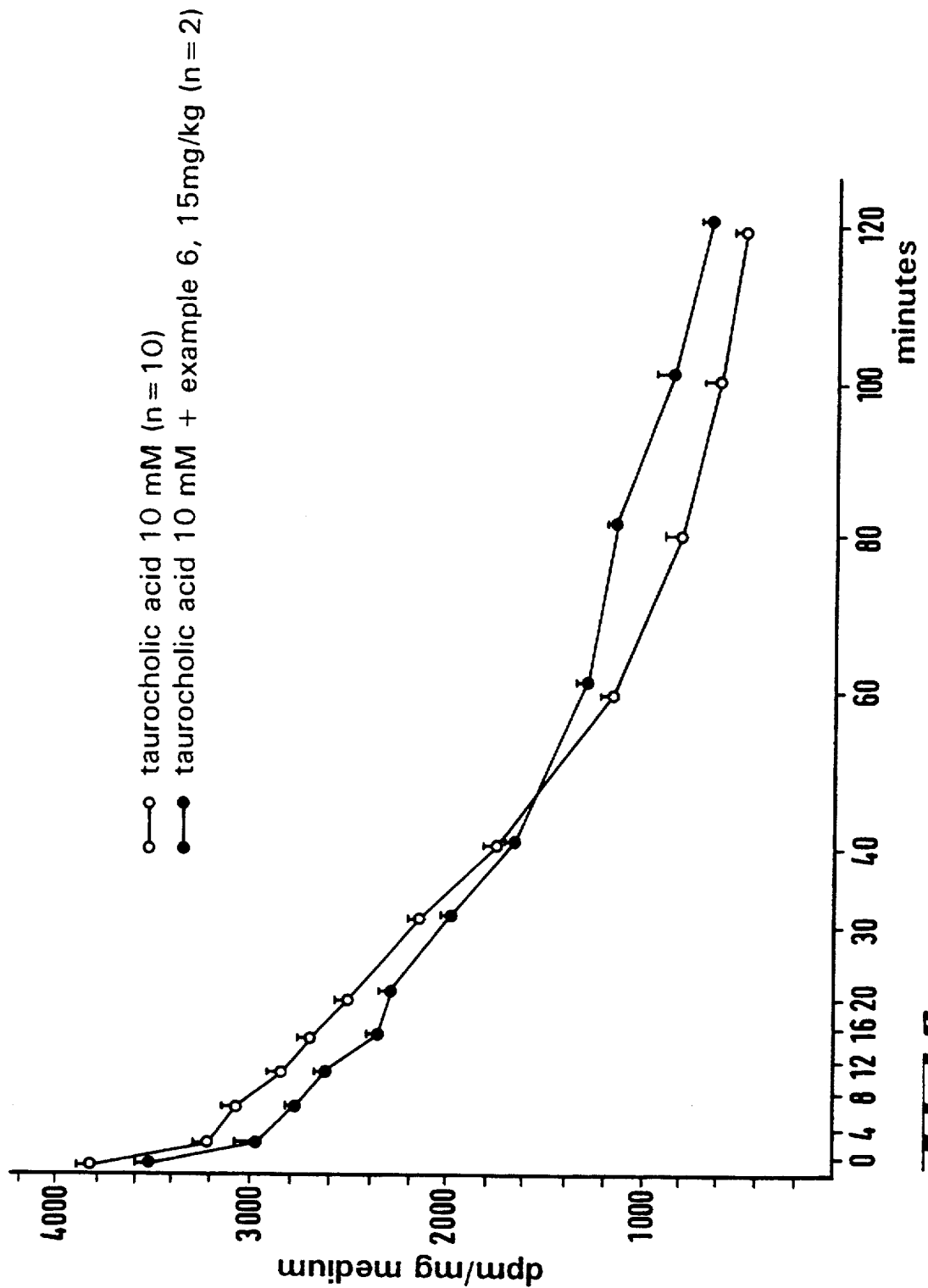

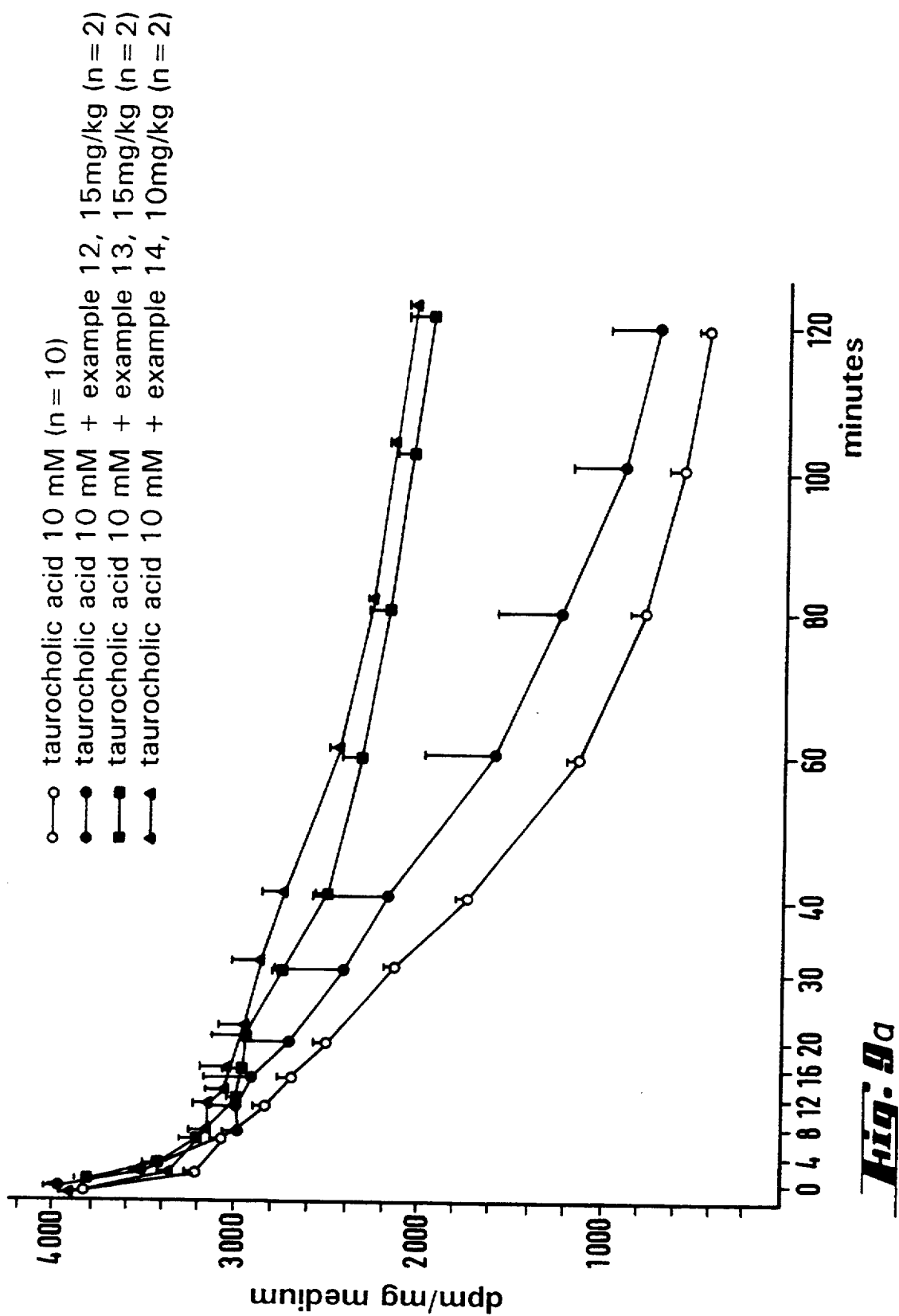

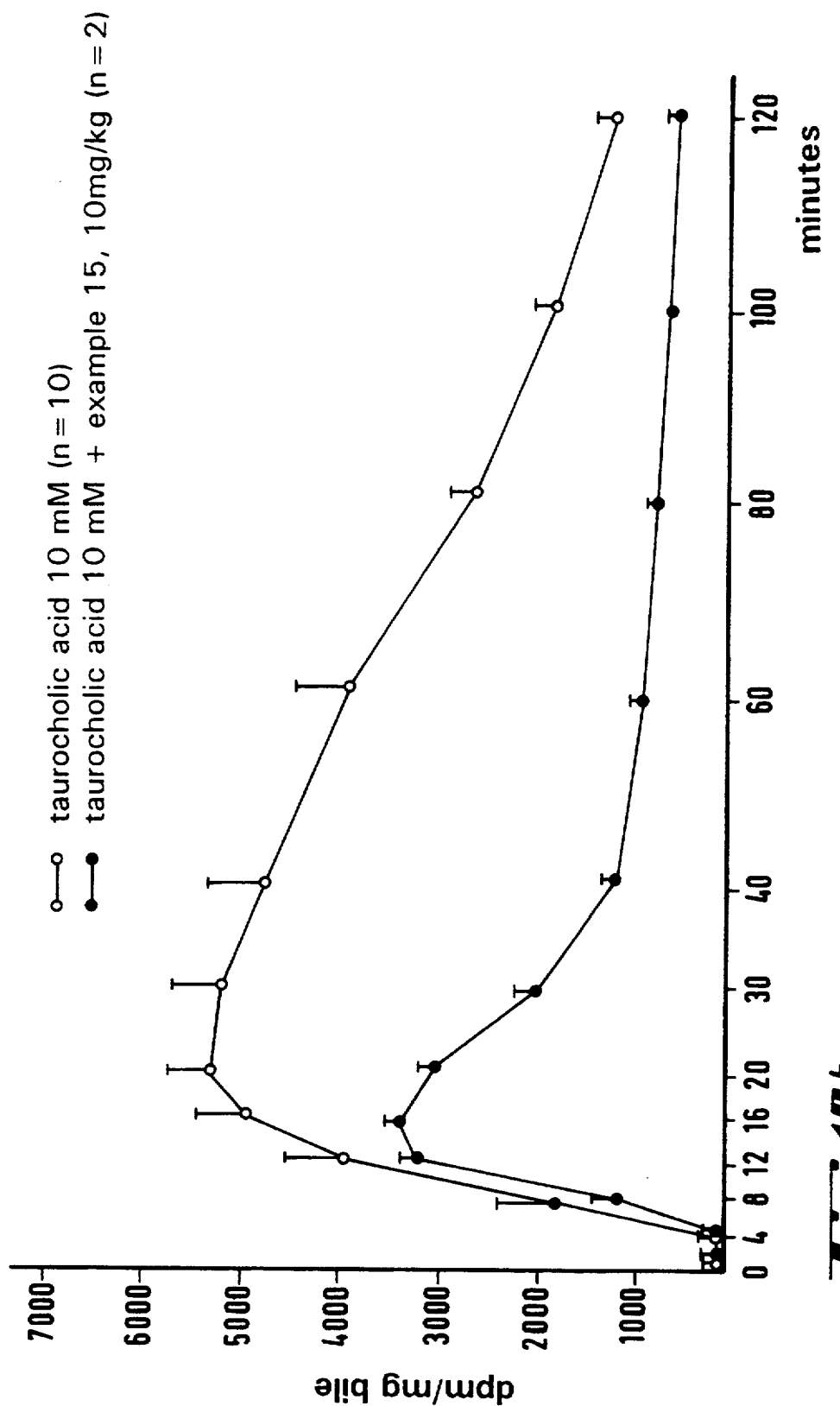

POLYMERS AND OLIGOMERS OF BILE ACID DERIVATIVES, PROCESS FOR THEIR PREPARATION AND THEIR USE AS PHARMACEUTICALS

The invention relates to polymers and oligomers of bile acids, a process for their preparation and their use as pharmaceuticals.

Bile acids and their salts are natural detergents and have an important physiological function in fat digestion, for example as cofactors of pancreatic lipases and in fat absorption. As the end products of cholesterol metabolism, they are synthesized in the liver, stored in the gall bladder and excreted from this by contraction into the small intestine, where they display their physiological action. The major part of the secreted bile acids is recovered again via the enterohepatic circulation. They pass back to the liver again via the mesenterial veins of the small intestine and the portal vein system.

In reabsorption in the intestine, both active and passive transport processes are important. In the terminal ileum, a specific $Na^+$-dependent transport system is responsible for bile acid reabsorption. In the enterohepatic circulation, the bile acids appear both as free acids, but also in the form of amino acid conjugates, such as glycine and taurine conjugates.

Non-absorbable, insoluble, basic and crosslinked polymers (resins) have been used-for some time for the binding of bile acids and have been used therapeutically on account of these properties. The subject of treatment is regarded as being all diseases in which an inhibition of bile acid reabsorption in the intestine, in particular in the small intestine, appears desirable. For example, chologenic diarrhea after resection of the ileum or alternatively increased cholesterol blood levels are treated in this manner. If the cholesterol blood level is increased, a reduction of this level can be achieved by intervention in the enterohepatic circulation.

By means of reduction of the bile acid pool found in the enterohepatic circulation, the corresponding de novo synthesis of bile acids from cholesterol in the liver is induced. To cover the cholesterol demand of the liver, resort is then had to the LDL-cholesterol (low density lipoprotein) found in the blood circulation, the hepatic LDL receptors acting in increased numbers. The acceleration of LDL catabolism thus effected acts through the reduction of the atherogenic cholesterol content in the blood.

Until now, the polymeric, basic insoluble and crosslinked ion exchange resins were the only possibility of influencing the enterohepatic circulation with respect to increased bile acid secretion and subsequent reduction in the cholesterol level (U.S. Pat. No. 3,383,281).

It was therefore the object of the present invention to seek further possibilities of influencing the enterohepatic circulation with respect to increased bile acid secretion without continuing the disadvantages of the resins employed hitherto.

The object is achieved by making available polymeric or oligomeric bile acids which can be prepared by polymerization of monomeric bile acids of the formula I $$G-X-A \qquad (I)$$

in which
G is a bile acid radical or derivative,
X is a bridge group and
A is a polymerizable, ethylenically unsaturated group, or by copolymerization with a monomer containing a polymerizable, ethylenically unsaturated double bond, in particular by copolymerization with a monomer of the formula IV

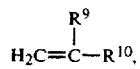   IV in which
$R^9$ is hydrogen or methyl and
$R^{10}$ is

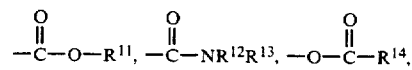

$-CN$, $-O-R^{15}$, hydrogen, halogen, in particular chlorine, bromine or iodine, $-SO_3H$ or $-O-(CH_2-CH_2O)_nR^{16}$,
in which
$R^{11}$ is hydrogen, $(C_1-C_{10})$-alkyl, $(C_1-C_{10})$-monohydroxyalkyl or $-(CH_2CH_2-O-)_nR^{16}$,
$R^{12}$, $R^{13}$, $R^{15}$ and $R^{16}$ are identical or different and are $(C_1-C_{10})$-alkyl,
$R^{14}$ is $(C_1-C_{18})$-alkyl and
n is 1 to 50, or by copolymerization with N-vinylpyrrolidone or its derivatives, and/or by copolymerization with ethylenically unsaturated dicarboxylic anhydrides and ethylenically unsaturated dicarboxylic acids each having 2 to 6 carbon atoms; their esters or half esters, esters being understood as meaning alkyl esters having 1–6 carbon atoms, cycloalkyl esters having 5 to 8 carbon atoms, benzyl esters or phenyl esters.

The term oligomers stands for homo-oligomers and cooligomers. The term polymers stands for homo-polymers and copolymers.

The compounds are crosslinked or non-crosslinked. Polymerization and copolymerization stand also for oligomerization and cooligomerization.

Among the compounds of the formula I, the following are preferred:
compounds in which
G is a free bile acid or its alkali metal or alkaline earth metal salt or a bile acid esterified on ring D and which is bonded via its ring A or B, preferably via ring A, to the group
X, to which the formula II preferably applies $$(Y)_o-(Z)_p \qquad (II),$$

in which
Y is adjacent to G and is $-O-$, $-NR'-$,

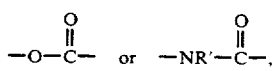

Z is $(C_1-C_{12})$-alkylene or $(C_7-C_{13})$-aralkylene, where individual methylene groups, preferably 1 to 4, in the alkylene chain of the alkylene or aralkylene radical can be replaced by groups such as $-O-$, $-NR'-$,

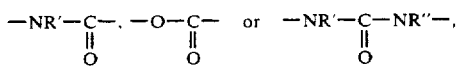

preferably a group of one type, o and p independently of one another are zero or 1, where o and p are not simultaneously zero, A is an ethylenically unsaturated group of the formula

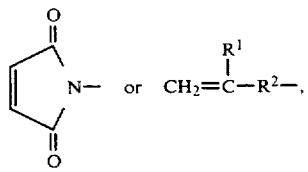

in which
$R^1$ is hydrogen or $CH_3$ and
$R^2$ is

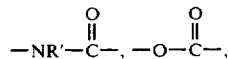

—O—C—, —O—, —NR'— or a single bond, where the carbonyl groups are adjacent to the C—C double bond, R' and R'' independently of one another are hydrogen or $(C_1-C_6)$-alkyl, preferably $(C_1-C_3)$-alkyl.

Among these, preferred polymers and oligomers are those in which G corresponds to the formula III

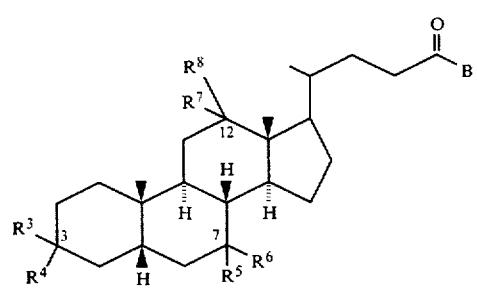

(III)

in which $R^3$ to $R^8$ independently of one another are hydrogen, OH, $NH_2$ or an OH group protected by an OH protective group and one of the radicals $R^3$ to $R^6$ is a bond to the group X, where this bond starts from the positions 3 ($R^3$ or $R^4$) or 7 ($R^5$ or $R^6$), preferably the β-position, and the other position 7 or 3 in each case carries an OH group or a protected OH group, is —OH, —O-alkali metal, —O-alkaline earth metal, —O—$(C_1-C_{12})$-alkyl, —O-allyl or —O-benzyl, preferably —OH, —O-alkali metal, —O—$(C_1-C_6)$-alkyl, —O-allyl or —O-benzyl, where alkyl is either n-alkyl or isoalkyl and where the ester group formed

is esters which can be hydrolyzed both by acid and by base,

Y is —O—, —NR'—,

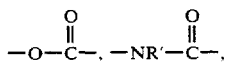

Z is $(C_1-C_{12})$-alkylene, $(C_7-C_{13})$-aralkylene, where 1 to 3 methylene groups in the alkylene chain are replaced by the groups —O—, —NR'—,

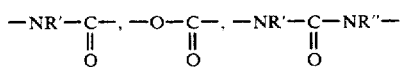

and o and p independently of one another are zero or 1, where o and p are not simultaneously zero, A is

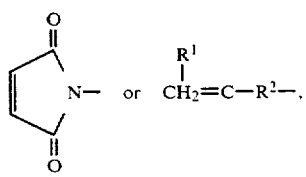

where
$R^1$ is hydrogen or $CH_3$ and
$R^2$ is

—NR'— or a single bond, in which
R' and R'' independently of one another are hydrogen or $(C_1-C_6)$-alkyl.

If p=zero and o=1, Y is preferably

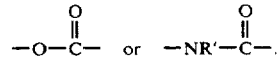

If p=1 and o=zero, Z is preferably $(C_1-C_{12})$-alkylene, where 1-3 methylene groups, preferably one methylene group, are replaced by

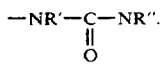

If p=1 and o=1, Y is preferably —O—. It is preferred here that Z is $(C_1-C_{12})$-alkylene or $(C_7-C_{13})$-aralkylene, where 1 or 2 methylene groups, preferably one methylene group, are replaced by

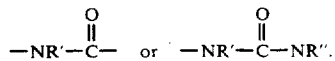

It is furthermore preferred here that one methylene group of Z is

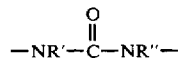

when Z itself is an aralkyl radical, in which the aryl radical is meta-linked, and Z on the one hand as the radical A carries a group

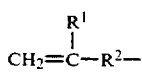

in which $R^2$ is a single bond and on the other hand carries a

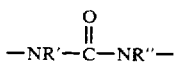

group which is meta-linked to the aralkylene radical via a methylene group.

It is also preferred here that, if Z is a $(C_1-C_{12})$alkylene group, at most one methylene group is replaced by

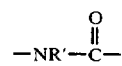

and the radical A is

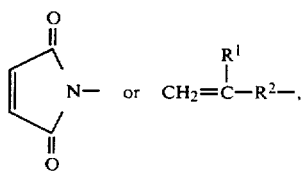

where $R^2$ is

.

It is furthermore particularly preferred that Y is not directly adjacent to the group replacing a methylene group of Z and also is not adjacent to

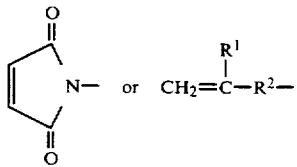

if $R^2$ is a single bond.

The compounds of the formula I are the subject of German Patent Application P 4142323.2 filed at the same time.

OH protective groups are understood as meaning an alkyl radical having 1–10 carbon atoms or an alkenyl radical having 2–10 carbon atoms, where the rings are branched or unbranched, a cycloalkyl radical having 3–8 carbon atoms, a phenyl radical which is unsubstituted or substituted 1–3 times by F, Cl, Br, $(C_1-C_4)$-alkyl or $(C_1-C_4)$-alkoxy, a benzyl radical which is unsubstituted or substituted 1–3 times by F, Cl, Br, $(C_1-C_4)$-alkyl or $(C_1-C_4)$-alkoxy or

radical, where R''' is hydrogen or $(C_1-C_4)$-alkyl.

Preferred comonomers of the formula IV are: (moth)acrylic acid, (meth)acrylic acid esters, acrylamide or acrylamide derivatives. Carboxylic acid vinyl esters having 3-20 carbon atoms and N-vinylpyrrolidone and its derivatives are particularly preferred. The monomers are optionally employed in a mixture.

The described polymers or copolymers of bile acid derivatives can additionally be crosslinked by copolymerization with ethylenically polyunsaturated monomers. Ethylenically diunsaturated or triunsaturated acrylic and methacrylic acid derivatives are preferably mentioned. The polymeric and oligomeric bile acids according to the invention can also be crosslinked by polymer-analogous reactions with bifunctional reagents generally used.

Suitable crosslinking agents are in particular the acid aides of the compounds mentioned and among these, in turn, acid amides of the formula V

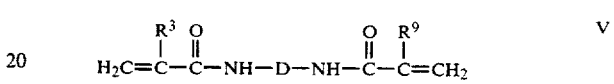

in which
$R^9$ is hydrogen or methyl and
D is $-(CHE)_m-$,
where
m is 1 to 10, preferably 2 to 4 and
E is hydrogen or OH, preferably hydrogen for m=2.

The invention furthermore relates to a process for the preparation of the polymeric bile acids.

The free radical polymerization or copolymerization is carried out in suspension or emulsion, or in substance, but preferably in solution using free radical initiators at temperatures below 250° C., preferably at temperatures from 40° to 100° C.

Suitable free radical initiators are inorganic or organic peroxides, percarbonates and azo compounds, which are preferably employed in amounts from 0.01 to 30 mol % with respect to that of monomers to be polymerized. The use of potassium peroxodisulfate, hydrogen peroxide, dilauryl peroxide is preferred or azobisisobutyronitrile, tert-butylperoxydiethyl acetate, dibenzoyl peroxide or tert-butoxy-2-ethyl hexanoate is particuarly preferred.

The following can furthermore be employed: tert-butyl peroxyisobutyrates, tert-butyl peroxyisopropyl carbonate, tert-butylperoxy-3,5,5-trimethylhexanoate, 2,2-bis(tert-butyl)peroxybutane, tert-butyl peroxystearyl carbonates, tert-butyl peroxyacetates, tert-butyl peroxybenzoate, dicumyl peroxide, 2,5-dimethyl-2,5-bis(tert-butylperoxy)hexane, tert-butyl cumyl peroxide, 1,3-bis(tert-butylperoxyisopropyl)benzene, di-tert-butyl peroxide, bis(2-methylbenzoyl) peroxide, bis(3,5,5-trimethylhexanoyl) peroxide, tert-butyl peroxypivalate, tert-amyl peroxypivalate, tert-butyl peroxyneodecanoate, tert-amyl peroxyneodecanoate, diisopropyl peroxydicarbonate, bis(2-ethylhexyl) peroxydicarbonate, di-n-butyl peroxydicarbonate, di-sec-butyl peroxydicarbonate and others.

The type of solvents employed depends on the solubility of the monomers employed. Water-soluble monomers are polymerized in aqueous solution. Monomers soluble in organic solvents can in principle be polymerized in all organic solvents in which free radical polymerizations are customarily carried out. Those employed are, for example, dimethyl sulfoxide, dimethylformamide, chloroform, methylene chloride, esters having up to 10 carbon atoms, for example ethyl acetate or methyl acetate or hydrocarbons such as benzene, toluene or xylene. Alcohols having up to 6 carbon atoms, for example methanol, ethanol, isopropanol, propanol and others as well as ethers such as, for example, tetrahydrofuran or dioxane are preferred. The solvents can optionally also be employed in a mixture or possibly in combination with water.

The molecular weight of the polymeric products can be controlled by the type and amount of the solvents employed and the free radical initiators used, by the reaction time and by the reaction temperature. Moreover, molecular weight control is possible by the use of regulators, preferably in amounts of up to 2 mol % with respect to the monomers employed, such as, for example, alkyl and aryl mercaptans, aldehydes, phenols and amines.

The polymers can be synthesized both by generally known metering methods and by the batch reaction.

The polymeric bile acids according to the invention have weight-average molecular weights of, preferably, up to 250,000 g/mol. Particularly preferred products are those having weight-average molecular weights between 2,000 and 100,000 g/mol, particularly preferred compounds are those whose molecular weight is between 3,000 and 60,000 g/mol.

In copolymeric compounds, the molar ratio of bile acid units to copolymerized monomer units should preferably be between 300:1 and 1:300, molar ratios of 150:1 to 1:150 are particularly preferred.

Polymeric bile acids of the type according to the invention containing hydrolyzable or transesterifyable units can be transesterified or hydrolyzed in solution to give the corresponding compounds. Suitable solvents here are preferably alcohols having up to 6 carbon atoms, ethers such as diethyl ether, tetrahydrofuran, dioxane, halohydrocarbons such as chloroform, methylene chloride, and moreover dimethyl sulfoxide or dimethylformamide.

Water-miscible solvents which can be employed in combination with water are particularly preferred. The hydrolyses are carried out with the addition of inorganic acids such as, for example, hydrochloric acid, sulfuric acid, or organic acids such as, for example, p-toluenesulfonic acid. However, the use of bases such as, for example, NaOH, KOH, prim. amines, sec. amines, tert. amines, alkali metal and alkaline earth metal alkoxides and others is preferred.

The hydrolyses are as a rule carried out at temperatures from 15° to 100° C.

The hydrolyzed polymers can be isolated and purified by chromatographic processes such as, for example, HPLC or GPC, by dialysis and subsequent lyophilization or by precipitation of the products from the reaction mixture.

The synthesis and properties of the polymeric bile acids according to the invention are illustrated in greater detail by the following examples. The examples shown do not restrict the subject matter of the invention in the slightest, but are to be understood as being a choice from the subject matter of the invention.

In the following examples, bile acid methyl esters of the formula VI are used.

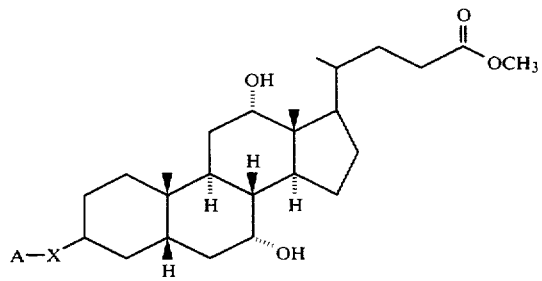

The group A—X is in each case defined in the examples.

For dialysis, Spectra/Por No. 3 dialysis tubing with an exclusion limit of 3,500 g/mol from Spectrum Medical Industries, INC. was employed.

The determination of the weight-average molecular weights was carried out by means of GPC in comparison with polystyrene standards.

Chromatograph: ALC/GPC 244 Waters chromatography
Column set: 4 ultrastyragel columns
Solvent: THF
Flow rate: 1 ml/min
Sample amount: 0.4 ml sample solution of c=0.2 g/dl
Detector: RI+4X

EXAMPLES

Example 1

In a reaction vessel, 1,000 mg of a bile acid methyl ester in which A—X is

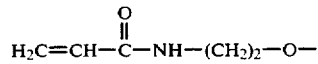

are dissolved under nitrogen in 4 ml of tetrahydrofuran and treated with 10 g of vinyl acetate and 300 mg of 75% strength dibenzoyl peroxide. The reaction mixture is heated at 80° C. with stirring for 6 hours. The reaction mixture is then treated with 15 ml of THF and the mixture is concentrated to dryness on a rotary evaporator. The residue is taken up in 25 ml of THF and treated under stirring with 2 ml of 10% strength methanolic sodium hydroxide solution and heated at 40° C. for 2 hours. The reaction mixture is then diluted with 50 ml of water, dialyzed against deionized water for 24 hours (cut-off: 3,500 g/mol) and lyophilized.

Molar ratio of bile acid units to vinyl alcohol units: 1:80 (determined by NMR), weight-average molecular weight of the unhydrolyzed substance: $M_w = 34,000$ g/mol (determined using GPC).

Example 2

In a reaction vessel, 3,000 mg of a bile acid methyl ester in which A—X is

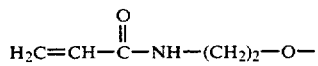

are dissolved under nitrogen in 4 ml of tetrahydrofuran and treated with 7 g of vinyl acetate and 300 mg of 75% strength dibenzoyl peroxide. The reaction mixture is heated at 80° C. with stirring for 6 hours. The reaction mixture is then treated with 15 ml of THF and the mixture is concentrated to dryness on a rotary evaporator. The residue is taken up in 25 ml of THF and treated under stirring with 2 ml of 10% strength methanolic sodium hydroxide solution and heated at 40° C. for 2 hours. The reaction mixture is then diluted with 50 ml of water, dialyzed against deionized water for 24 hours (cut-off: 3,500 g/mol) and lyophilized.

Molar ratio of bile acid units to vinyl alcohol units: 1:12.5 (determined by NMR), weight-average molecular weight of the unhydrolyzed substance: $M_w=8,000$ g/mol (determined using GPC).

Example 3

In a reaction vessel, 4,920 mg of a bile acid methyl ester, where A—X is

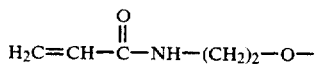

are dissolved in 4 ml of tetrahydrofuran under nitrogen and treated with 220 mg of 75% strength dibenzoyl peroxide, dissolved in 0.3 ml of THF and 0.2 ml of methanol. The reaction mixture is heated at 80° C. with stirring. 17.01 g of N-vinylpyrrolidone are continuously metered into the reaction mixture in the course of 4 hours, after 2 and after 4 hours reaction time in each case 220 mg of 75% strength dibenzoyl peroxide, dissolved in 0.3 ml of THF and 0.2 ml of methanol, being added. After metering in of the N-vinylpyrrolidone has taken place, the mixture is allowed to react at 80° C. for 2 hours. The reaction mixture is then diluted with 15 ml of THF and treated with 0.5 ml of 20% strength aqueous sodium hydroxide solution. After about 10 minutes, the turbidity of the reaction mixture which occurs is removed by addition of water, and this process is repeated until turbidity of the mixture no longer occurs. The reaction mixture is then diluted with 50 ml of water, dialyzed against deionized water for 24 hours (cut-off: 3,500 g/mol) and lyophilized.

Molar ratio of bile acid units to N-vinylpyrrolidone units: 1:1 (determined by NMR), weight-average molecular weight of the unhydrolyzed substance: $M_w=38,000$ g/mol (determined using GPC).

Example 4

In a reaction vessel, 3,000 mg of a bile acid methyl ester, where A—X is

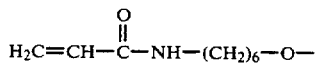

are dissolved in 4 ml of tetrahydrofuran under nitrogen and treated with 120 mg of 75% strength dibenzoyl peroxide, dissolved in 0.4 ml of toluene. The reaction mixture is heated at 80° C. with stirring. 17.01 g of N-vinylpyrrolidone are continuously metered into the reaction mixture in the course of 4 hours, after 2 and after 4 hours reaction time in each case 120 mg of 75% strength dibenzoyl peroxide, dissolved in 0.4 ml of toluene, being added. After metering in of the N-vinylpyrrolidone has taken place, the mixture is allowed to react at 80° C. for 2 hours. The reaction mixture is then diluted with 15 ml of THF and treated with 0.5 ml of 20% strength aqueous sodium hydroxide solution. After about 10 minutes, the turbidity of the reaction mixture which occurs is removed by addition of water, and this process is repeated until turbidity of the mixture no longer occurs. The reaction mixture is then diluted with 50 ml of water, dialyzed against deionized water for 24 hours (cut-off: 3,500 g/mol) and lyophilized.

Molar Ratio of bile acid units to N-vinylpyrrolidone units: 2:3 (determined by NMR), weight-average molecular weight of the unhydrolyzed substance: $M_w=16,000$ g/mol (determined using GPC).

Example 5

In a reaction vessel, 1,110 mg of a bile acid methyl ester, in which A—X is

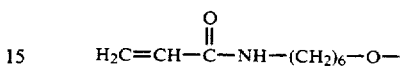

are dissolved in 8 ml of tetrahydrofuran under nitrogen and treated with 150 mg of 75% strength dibenzoyl peroxide, dissolved in 0.75 ml of toluene. The reaction mixture is heated at 75° C. with stirring for 18 hours. The reaction mixture is then diluted with 10 ml of THF and treated with 0.5 ml of 20% strength aqueous sodium hydroxide solution. After about 10 minutes, the turbidity of the reaction mixture which occurs is removed by addition of water. This process is repeated until turbidity of the mixture no longer occurs. The reaction mixture is then diluted with 30 ml of water, dialyzed against deionized water for 24 hours (cut-off: 3,500 g/mol) and lyophilized.

Weight-average molecular weight of the unhydrolyzed substance: $M_w=10,000$ g/mol (determined using GPC).

Example 6

In a reaction vessel, 386.8 mg of a bile acid methyl ester, in which A—X is

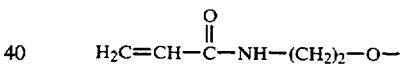

are dissolved in 2.78 ml of tetrahydrofuran under nitrogen and treated with 52 mg of 75% strength dibenzoyl peroxide, dissolved in 0.5 ml of toluene. The reaction mixture is heated at 75° C. with stirring for 18 hours. The reaction mixture is then diluted with 10 ml of THF and treated with 0.5 ml of 20% strength aqueous sodium hydroxide solution. After about 10 minutes, the turbidity of the reaction mixture which occurs is removed by addition of water. This process is repeated until turbidity of the mixture no longer occurs. The reaction mixture is then diluted with 30 ml of water, dialyzed against deionized water for 24 hours (cut-off: 3,500 g/mol) and lyophilized.

Weight-average molecular weight of the unhydrolyzed substance: $M_w=11,000$ g/mol (determined using GPC).

Example 7

In a reaction vessel, 340 mg of a bile acid methyl ester, in which A—X is

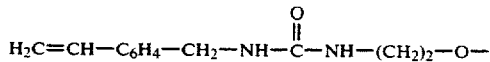

are dissolved in 2.4 ml of tetrahydrofuran under nitrogen and treated with 45 mg of 75% strength dibenzoyl peroxide, dissolved in 0.5 ml of toluene. The reaction mixture is heated at 75° C. with stirring for 18 hours. The reaction mixture is then diluted with 10 ml of THF and treated with 0.5 ml of 20% strength aqueous sodium hydroxide solution. After about 10 minutes, the turbidity of the reaction mixture which occurs is removed by addition of water. This process is repeated until turbidity of the mixture no longer occurs. The reaction mixture is then diluted with 30 ml of water, dialyzed against deionized water for 24 hours (cut-off: 3,500 g/mol ) and lyophilized.

Example 8

In a reaction vessel, 558.8 mg of a bile acid methyl ester, in which A—X is

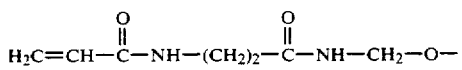

are dissolved in 4 ml of tetrahydrofuran under nitrogen and treated with 74.5 mg of 75% strength dibenzoyl peroxide, dissolved in 0.8 ml of toluene. The reaction mixture is heated at 75° C. for 18 hours with stirring. The reaction mixture is then diluted with 10 ml of THF and treated with 0.5 ml of 20% strength aqueous sodium hydroxide solution. After about 10 minutes, the turbidity of the reaction mixture which occurs is removed by addition of water. This process is repeated until turbidity of the mixture no longer occurs. The reaction mixture is then diluted with 30 ml of water, dialyzed against deionized water for 24 hours (cut-off: 3,500 g/mol) and lyophilized.

Weight-average molecular weight of the unhydrolyzed substance: $M_w = 14,000$ g/mol (determined using GPC).

Example 9

In a reaction vessel, 437.4 mg of a bile acid methyl ester, in which A—X is

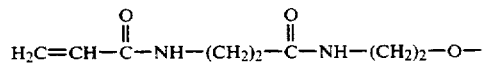

are dissolved in 3.2 ml of tetrahydrofuran under nitrogen and treated with 62.7 mg of 75% strength dibenzoyl peroxide, dissolved in 0.7 ml of toluene. The reaction mixture is heated at 75° C. for 18 hours with stirring. The reaction mixture is then diluted with 10 ml of THF and treated with 0.5 ml of 20% strength aqueous sodium hydroxide solution. After about 10 minutes, the turbidity of the reaction mixture which occurs is removed by addition of water. This process is repeated until turbidity of the mixture no longer occurs. The reaction mixture is then diluted with 30 ml of water, dialyzed against deionized water for 24 hours (cut-off: 3,500 g/mol) and lyophilized.

Weight-average molecular weight of the unhydrolyzed substance: $M_w = 13,000$ g/mol (determined using GPC).

Example 10

The example is carried out in accordance with Example 9, but the following compounds are employed:

424 mg of bile acid methyl ester in 3 ml of THF, in which A—X is

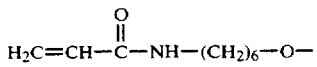

0.424 mg of dodecyl mercaptan in 50 μl of THF as a regulator and 56.52 mg of dibenzoyl peroxide (BSO), 75% strength, in 563.7 μl of toluene.

The product obtained has a weight-average molecular weight of the unhydrolyzed substance of $M_w = 6,900$ g/mol (determined using GPC).

Example 11

The example is carried out in accordance with Example 9, but the following compounds are employed:

400 mg of bile acid methyl ester in 2.9 ml of THF, in which A—X is

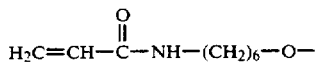

and 5.39 mg of BSO, 75% strength, in 53.8 μl of toluene.

The product obtained has a weight-average molecular weight of the unhydrolyzed substance of $M_w = 8,800$ g/mol (determined using GPC).

Example 12

The example is carried out in accordance with Example 9, but the following compounds are employed:

407.3 mg of bile acid methyl ester in 2.95 ml of THF, in which A—X is

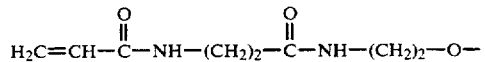

1.53 mg of glyoxal bisacrylamide in 74.6 μl of methanol as crosslinking agent and 58.4 mg of BSO, 75% strength, in 582.4 μl of toluene.

The product obtained in each case has an average molecular weight of the unhydrolyzed substance of $M_w = 5,400$ g/mol (determined using GPC).

Example 13

The example is carried out in accordance with Example 9, but the following compounds are employed:

409 mg of bile acid methyl ester in 2.95 ml of THF, in which A—X is

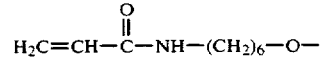

and 54.53 mg of BSO, 75% strength, in 543.8 μl of toluene.

The product obtained has a weight-average molecular weight of the unhydrolyzed substance of $M_w = 7,500$ g/mol (determined using GPC).

Example 14

The example is carried out in accordance with Example 9, but the following compounds are employed:

400.7 mg of bile acid methyl ester in 2.9 ml of THF, in which A—X is

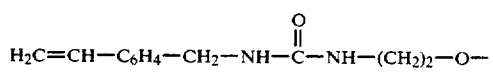

1.5 mg of glyoxal bisacrylamide as crosslinking agent in 70 μl of methanol and 53.4 mg of BSO, 75% strength, in 529 μl of toluene.

Example 15

The example is carried out in accordance with Example 9, but the following compounds are employed:

416.3 mg of bile acid methyl ester in 2.9 ml of THF, in which A—X is

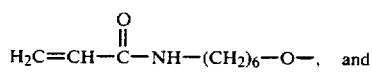

0.81 mg of tert-butyl peroxydiethyl acetate as initiator in 15.5 μl of THF, reaction time 21 h.

The product obtained has a weight-average molecular weight of the unhydrolyzed substance of $M_w = 10{,}700$ g/mol (determined using GPC).

In in-vitro and in-vivo investigations of the compounds of the polymeric bile acid type according to the invention, which have a high affinity for the bile acid transport system, it has surprisingly been found that these compounds inhibit bile acid absorption in a concentration-dependent manner. It was furthermore possible to show that the compounds according to the invention are not absorbed themselves and thus do not pass into the enterohepatic circulation. As a result of this knowledge, it is now possible to intervene in the enterohepatic circulation with greater efficiency than was hitherto possible using the resins.

In the case of the resins already obtainable as pharmaceuticals, for example colestyramine (contains quaternary ammonium groups) or colestipol (contains secondary or tertiary amino groups), the expedient daily dose is very high. For example, for colestyramine it is 12–24 g, highest daily dose 32 g. The recommended dose is 15–20 g. Furthermore, taste, odor and the high dosage make patient compliance difficult. The known side effects (for example avitaminoses) of the resins are attributed to lack of selectivity. These side effects must also be taken into account in the dosage of simultaneously administered medicaments, but also in the case of bile acid depletion, which is caused by various gastrointestinal disorders (obstipation, steatorrhea) to a differing degree.

For colestyramine and colestipol, therapeutic importance as a result of combination with other hypolipidemic pharmaceuticals such as fibrates, HMG-CoA reductase inhibitors, probucol (cf., for example, M. N. Cayen, Pharmac. Ther. 29, 187 (1985) and 8th International Symposium on Atherosclerosis, Rome, Oct. 9–13, 1988, Abstracts P. 544, 608,710) was described, the effects obtained also making possible the therapy of severe hyperlipidemias. But the following features of said preparations and in particular of, for example, colestipol were to be regarded as worthy of improvement:

1. The high daily doses, which can be attributed to a relatively low binding rate at neutral pH in isotonic medium and the (partial) re-release of the adsorbed bile acids.
2. The qualitative shift in the bile acid composition of the bile with a decrease in tendency for chenodeoxycholic acid and the increasing risk of cholelithiasis associated therewith.
3. The lack of a damping action on the cholesterol metabolism of the intestinal bacteria.
4. The excessively high binding rate of vitamins and pharmaceuticals makes a need for a substitute for these substances and blood level controls possibly necessary.
5. The current administration form is to be regarded as unsatisfactory.

By means of inhibition of bile acid re-absorption with the aid of the polymeric bile acids according to the invention in the small intestine, the bile acid concentration found in the enterohepatic circulation is reduced in an essentially more effective manner, so that a fall in the cholesterol level in the serum takes place. Avitaminoses are seen just as little when using the compounds according to the invention as is the effect on the absorption of other pharmaceuticals. Nor is there a negative effect on the intestinal flora, since the binding of the polymers according to the invention to the intestinal mucous membrane is extremely stable and persists very long after binding has taken place.

It is additionally to be expected that the known side effects (obstipation, steratorrhea) are not observed.

Finally, the use of high doses does not lead to cell damage. The dose of the resins which is otherwise usual can therefore be considerably reduced by use of the compounds according to the invention. The recommended dose is appropriately up to 10 g per day, preferably 0,1 to 5,0 g/day, in particular 0,3 to 5,0 g/day.

The following methods were used:

| HPLC with FLUORESCENCE DETECTION | |
|---|---|
| Equipment: | HPLC unit from Kontron, consisting of three pumps and mixing chamber, autosampler, UV detector and analysis unit with MT2 software. Merck-Hitachi fluorescence detector. Since the samples are light- and heat-sensitive, the autosampler is cooled to about 5° C. |
| Mobile phase: | Eluent A: ®Millipore water (in-house unit) Eluent B: acetonitrile/methanol 60:30 |
| Column: | ®LiChrospher 100 RP-18, 25 mm, 5 μm from Merck |
| Precolumn: | LiChrospher 60 RP-select B, 4 mm, 5 μm from Merck |
| Flow rate: | 1.3 ml/min |
| Mobile Phase: | Eluent A: ammonium carbamate buffer 0.019 M, adjusted to pH 4.0 with phosphoric acid. Eluent B: acetonitrile |
| Column: | LiChrospher 100 RP-8, 25 mm, 5 μm from Merck |
| Precolumn: | LiChrospher 60 RP-select B, 4 mm, 5 μm from Merck |
| Flow rate: | Gradient: 0.00 min 0.8 ml/min  20.00 min 0.8 ml/min  23.00 min 1.3 ml/min  51.00 min 1.3 ml/min |
| Detection: | 200 nm (for preparations additionally at 254 nm) |
| Gradient: | 0.00 min 32% B  8.00 min 35% B  17.00 min 38% B  20.00 min 40% B  24.00 min 40% B  30.00 min 50% B  45.00 min 60% B |

Enzymatic determination of the total bile acid

900 μl each of the following mixture are added to Eppendorf vessels:

6 ml of tetrasodium diphosphate buffer 0.1M, pH 8.9,
2 ml of NAD solution (4 mg/ml water),
20 ml of Millipore water 30 μl of the sample and 30 μl of enzyme solution are added to this by pipette.

Enzyme solution: 3-alpha-hydroxysteroid dehydrogenase 0.5 units/ml

The batches are mixed and incubated at room temperature for 2 h.

Subsequently transfer to 1 ml disposable cuvettes and measurement in a photometer at 340 nm.

Only of limited suitability for bile samples, since the green color interferes.

| HPLC with UV DETECTION | |
|---|---|
| Equipment: | HPLC unit from Kontron, consisting of three pumps and mixing chamber, autosampler, UV detector and analysis unit with MT2 software. |
| Mobile phase: | Eluent A: ammonium carbamate buffer 0.019 M, adjusted to pH 4.0 with phosphoric acid. |
| | Eluent B: acetonitrile |
| Column: | LiChrospher 100 RP-18, 25 mm, 5 μm from Merck |
| Precolumn: | LiChrospher 60 RP-select B, 4 mm, 5 μm from Merck |
| Flow rate: | Gradient: 0.00 min 0.8 ml/min |
| | 20.00 min 0.8 ml/min |
| | 23.00 min 1.3 ml/min |
| | 51.00 min 1.3 ml/min |
| Detection: | 200 nm (for preparations additionally at 254 nm) |
| Gradient: | 0.00 min 32% B |
| | 8.00 min 35% B |
| | 17.00 min 38% B |
| | 20.00 min 40% B |
| | 24.00 min 40% B |
| | 30.00 min 50% B |
| | 45.00 min 60% B |

The in vivo investigation was carried out as described in F. G. J. Poelma et al. (J. Pharm. Sci. 78 (4), 285–89, 1989) with some modifications.

In the investigations, taurocholate and taurocholic acid or cholate and cholic acid are used synonymously.

Cannulation of the Bile Duct

The bile duct is dissected free and a catheter is tied in (PE 50, Intramedic ®). An adaptor for admitting 100 μl disposable pipette tips (Brandt) was attached to its end. The bile is collected in these pipettes and transferred to weighed Eppendorf reaction vessels after specific time intervals. After the end of the experiment, the bile, as well as the medium samples, is weighed and aliquots are measured in a scintillation counter. For this purpose, 10 μl samples are pipetted into a Sarstedt sample vessel, 58×22 mm, mixed with 10 ml of Quickszint 212 (Zinsser GmbH, Frankfurt am Main, Germany) and counted in a Beckman 2800 β-counter after a 30 min decay period.

1. The compounds according to the invention, Examples 1 to 15, were instilled into the intestinal segment together with 10 mM taurocholate containing $^3$H-taurocholate or $^{14}$C-taurocholate as tracer and the perfusion solution was circulated for 2 h with the aid of a peristaltic pump. The decrease of the tracer in the intestine (medium) and the appearance of the tracer in the bile fluid (bile) was determined with the aid of scintillation measurements and HPLC. As a control, 10 mM taurocholate which tracer and without a compound of the invention was instilled and the change in the intestine and in the bile fluid was determined (FIGS. 1a–10a and 1b–10b)

2. In vivo perfused intestine

The experimental animals used are Wistar rats bred in-house (animal-holding Hoechst) having, on average, a body weight of 230–290 g. The experimental animals are not fasted before anesthesia (urethane 1 g/kg i.p.). After onset of anesthesia, the animals are immobilized on a temperature-adjustable (constant 37° C.). OP bench (Medax), shaved on the ventral side and the abdominal wall of the animals is then opened using a cut about 7 cm long. A Luer adaptor (Hoechst Precision Engineering) is then tied into the lower small intestine about 8 cm from the ileocaecal valve, the secondary small intestine being tied off in this way. A further tying into and tying off of the small intestine is then carried out 13–14 cm from the start of the small intestine. The contents of this intestinal segment are carefully washed out with 37° C. isotonic saline solution. The test solution is later instilled into this segment, the end part of the jejunum—start of the ileum.

The pump tubing is first filled from the 2 ml of instillation solution (10 mM taurocholate, preparation in the given concentration, tracer: 3.5 μCi [$^3$H(G)]-taurocholic acid, NET-322, lot 2533-081, DuPont de Nemour GmbH, Dreieich, Germany) dissolved in phosphate-buffered isotonic saline solution (silicone tubing A, 0.5 mm Desaga, Heidelberg, Germany, Order No. 132020). The pump tubing is then attached to the intestinal segment using two Luer adaptors and the remaining solution is added by means of a three-way valve (Pharmaseal 75a) and a 2 ml disposable syringe (Chirana). Immediately after this, the peristaltic pump (LKB Multiperpex 2115) is switched on, and the medium is circulated at 0.25 ml/min. At regular intervals, a sample for measurement of the activity (decrease in radioactivity in the intestine = absorption rate) is removed from an infusion tube integrated in the circulation by means of a Hamilton syringe and a cannula (Termo 0.4×20).

Figure 11A:
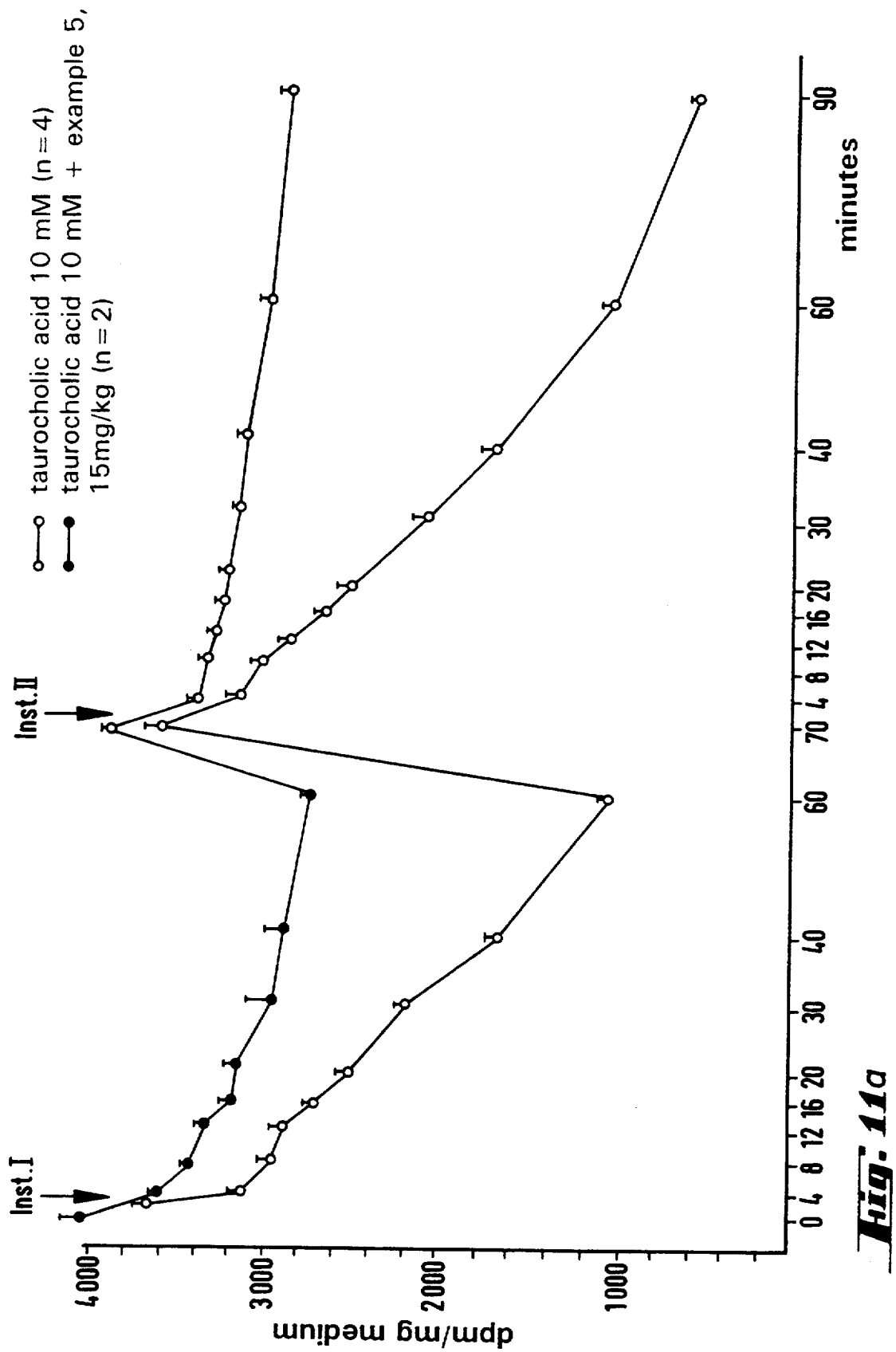
Figure 11B:
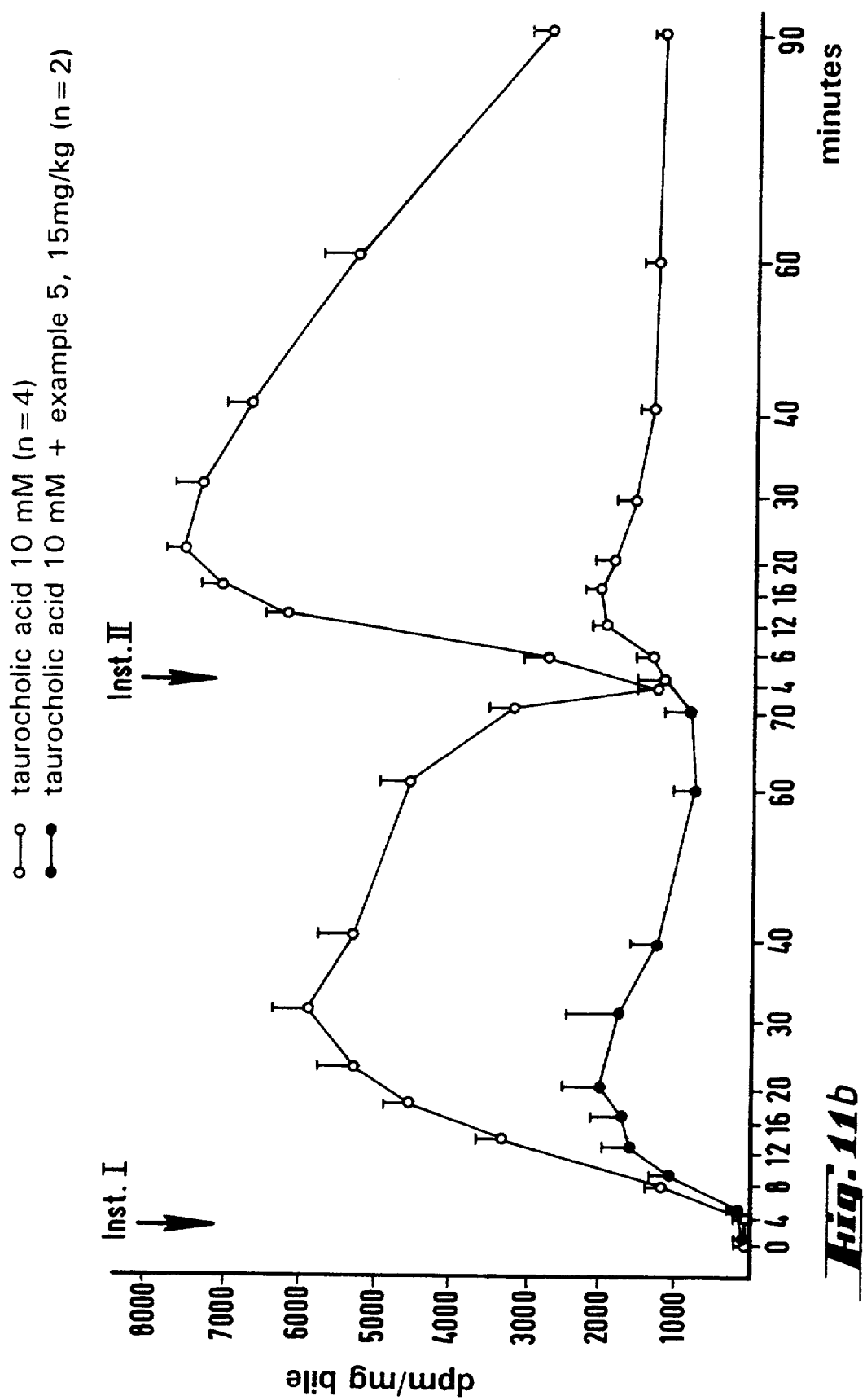

To detect the prolonged effect of the oligomeric or polymeric bile acids (FIGS. 11a+b), in this special test design the outflow (intestine) and the filling (bile) of the radioactive tracer were tested during the first (inst. I) instillation with inhibitor and during the second instillation (inst. II) without the inhibitor.

We claim:

1. A polymeric or oligomeric bile acid, prepared by polymerization of a monomeric bile acid of the formula I

$$G—X—A \qquad (I)$$

in which
G is a free bile acid or its alkali metal salt or a bile acid having rings A, B, C, D esterified on ring D and which is bonded via its ring A, B or C, to the group X, X is a bridge group and A is a polymerizable, ethylenically unsaturated group, or by copolymerization with a monomer containing a polymerizable, ethylenically unsaturated double bond, or by copolymerization with N-vinylpyrrolidone or its derivatives, and/or by copolymerization with ethylenically unsaturated dicarboxylic anhydrides and ethylenically unsaturated dicarboxylic acids each having 2 to 6 carbon atoms; their esters or half esters, esters being understood as alkyl esters having 1-6 carbon atoms, cycloalkyl esters having 5 to 8 carbon atoms, benzyl esters or phenyl esters.

2. A polymer or oligomer as claimed in claim 1, wherein

G is a free bile acid or its alkali metal salt or a bile acid esterified on ring D and which is bonded via its ring A, B or C, to the group X, to which the formula II applies $$(Y)_o-(Z)_p \quad (II)$$

in which

Y is adjacent to G and is —O—, —NR'—, $$-O-\underset{O}{\overset{\parallel}{C}}-, \quad \text{or} \quad -NR'-\underset{O}{\overset{\parallel}{C}}-,$$

is $(C_1\text{-}C_{12})$-alkylene or $(C_7\text{-}C_{13})$-aralkylene, where individual methylene groups in the alkylene chain of the alkylene or aralkylene radical can be replaced by one or more groups selected from —O—, —NR'—, $$-NR'-\underset{O}{\overset{\parallel}{C}}-, \quad -O-\underset{O}{\overset{\parallel}{C}}- \quad \text{and} \quad -NR'-\underset{O}{\overset{\parallel}{C}}-NR''-,$$

o and p independently of one another are zero or 1, where o and p are not simultaneously zero, A is an ethylenically unsaturated group of the formula

[structure: maleimide ring with N—] or $CH_2=\overset{R^1}{\underset{|}{C}}-R^2-$, in which $R^1$ is hydrogen or $CH_3$ and $R^2$ is $$-NR'-\underset{O}{\overset{\parallel}{C}}-, \quad -O-\underset{O}{\overset{\parallel}{C}}-,$$

—O—, —NR'— or a single bond, where the carbonyl groups are adjacent to the C—C double bond, R' and R'' independently of one another are hydrogen or $(C_1\text{-}C_6)$-alkyl.

3. A polymer or oligomer as claimed in claim 2, wherein

G corresponds to the formula III

[steroid structure with labels $R^3$, $R^4$, $R^5$, $R^6$, $R^7$, $R^8$, positions 3, 7, 12, and —C(O)B group] (III)

in which $R^3$ to $R^8$ independently of one another are hydrogen, OH, $NH_2$ or an OH group protected by an OH protective group and one of the radicals $R^3$ to $R^6$ is a bond to the group X, where this bond starts from the positions 3 ($R^3$ or $R^4$) or 7 ($R^5$ or $R^6$), and the other position 7 or 3 in each case carries an OH group or a protected OH group, B is —OH, —O-alkali metal, —O-alkaline earth metal, —O—$(C_1\text{-}C_{12})$-alkyl, —O-allyl or —O-benzyl where alkyl is either n-alkyl or iso-alkyl and where the ester group formed $$\overset{O}{\underset{}{\overset{\parallel}{\diagup}}}{}_B$$

is an ester which can be saponified both by acid and by base,

Y is —O—, —NR'—, $$-O-\underset{O}{\overset{\parallel}{C}}-, \quad \text{or} \quad -NR'-\underset{O}{\overset{\parallel}{C}}-,$$

Z is $(C_1\text{-}C_{12})$-alkylene, $(C_7\text{-}C_{13})$-aralkylene, where 1 to 3 methylene groups in the alkylene chain are replaced by the groups —O—, —NR', $$-NR'-\underset{O}{\overset{\parallel}{C}}-, \quad -O-\underset{O}{\overset{\parallel}{C}}-, \quad \text{or} \quad -NR'-\underset{O}{\overset{\parallel}{C}}-NR''-$$

and o and p independently of one another are zero or 1, where o and p are not simultaneously zero, A is

[structure: maleimide ring with N—] or $CH_2=\overset{R^1}{\underset{|}{C}}-R^2-$, where $R^1$ is hydrogen or $CH_3$ and $R^2$ is $$-NR'-\underset{O}{\overset{\parallel}{C}}-,$$

—NR'— or a single bond, in which R' and R'' independently of one another are hydrogen or $(C_1\text{-}C_6)$-alkyl.

4. The polymeric or oligomeric bile acid of claim 1, wherein said monomer containing a polmerizable, ethylenically unsaturated double bond is a monomer of formula IV $$H_2C=\overset{R^9}{\underset{|}{C}}-R^{10}$$ (IV)

in which
R$^9$ is hydrogen or methyl and
R$^{10}$ is $$-\overset{O}{\underset{\|}{C}}-O-R^{11}, \quad -\overset{O}{\underset{\|}{C}}-NR^{12}R^{13}, \quad -O-\overset{O}{\underset{\|}{C}}-R^{14},$$

—CN, —O—R$^{15}$, hydrogen halogen —SO$_3$H, or —O—(CH$_2$—CH$_2$O)$_n$R$^{16}$,
in which
R$^{11}$ is hydrogen, (C$_1$-C$_{10}$)-alkyl, (C$_1$-C$_{10}$)-monohydroxyalkyl or —(CH$_2$CH$_2$—O—)$_n$R$^{16}$,
R$^{12}$, R$^{13}$, R$^{15}$, and R$^{16}$ are identical or different and are (C$_1$-C$_{10}$)-alkyl,
R$^{14}$ is (C$_1$-C$_{18}$)-alkyl and
n is 1 to 50.

5. A polymer or oligomer as claimed in claim 1, wherein the weight-average molecular weight is up 250,000 g/mol.

6. A polymer or oligomer as claimed in claim 1, wherein in the case of copolymers the molar ratio of bile acid units to copolymerized monomer units is between 300:1 and 1:300.

7. A polymer or oligomer as claimed in claim 1, wherein the crosslinking is carried out by means of copolymerization with ethylenically polyunsaturated monomers.

8. A polymer or oligomer as claimed in claim 7, wherein the crosslinking is carried out with ethylenically polyunsaturated acrylic acid and methacrylic acid derivatives.

9. A polymer or oligomer as claimed in claim 7, wherein the crosslinking is carried out with acid amides of the formula V $$H_2C=\overset{R^9}{\underset{|}{C}}-\overset{O}{\underset{\|}{C}}-NH-D-NH-\overset{O}{\underset{\|}{C}}-\overset{R^9}{\underset{|}{C}}=CH_2 \quad V$$

in which
R$^9$ is hydrogen or methyl and
D is —(CHE)$_m$—,
where
m is 1 to 10 and
E is hydrogen or OH.

10. A pharmaceutical composition comprising a compound of claim 1 and a pharmaceutically acceptable carrier.

11. The polymer or oligomer as claimed in claim 5, wherein the weight-average molecular weight is between 2,000 and 100,000 g/mol.

12. The polymer or oligomer as claimed in claim 12, wherein the weight-average molecular weight is between 3,000 and 60,000 g/mol.

13. The polymer or oligomer as claimed in claim 3, wherein B is —OH, —O-alkali metal, —O—(C$_1$-C$_6$)-alkyl, —O-allyl or —O-benzyl.

14. The polymer or oligomer as claimed in claim 3, wherein R$^3$ to R$^8$ independently of one another are hydrogen, OH, NH$_2$ or an OH group protected by an OH protective group and one of the radicals R$^3$ to R$^6$ is a bond to the group X, where this bond starts from the positions 3 (R$^3$ or R$^4$) or 7 (R$^5$ or R$^6$) in the $\beta$-position, and the other position 7 or 3 in each case carries an OH group or a protected OH group.

15. The polymer or oligomer as claimed in claim 2, wherein G is a free bile acid or its alkali metal salt or a bile acid esterfied on ring D which is bonded via its ring A to the group X.

16. A polymer or oligomer as claimed in claim 4, wherein the monomers are compounds according to the formula IV (meth)acrylic acid, (meth)acrylic acid esters, acrylamide and its derivatives, carboxylic acid vinyl esters having 3-20 carbon atoms or N-vinylpyrrolidone and its derivatives.

17. The polymeric or oligomeric bile acid of claim 4, wherein said halogen is chlorine, bromine, or iodine.

* * * * *

UNITED STATES PATENT AND TRADEMARK OFFICE
CERTIFICATE OF CORRECTION

PATENT NO. : 5,430,116
DATED : July 04, 1995
INVENTOR(S) : Werner KRAMER et al

It is certified that error appears in the above-indentified patent and that said Letters Patent is hereby corrected as shown below:

Claim 2, Column 17, Line 28, insert --Z-- before "is", and change "$(C_{1-C12})$" to --$(C_1-C_{12})$--.

Claim 3, Column 18, Line 16, change "$NH_2or$" to --$NH_2$ or--;

Line 19, change "$R_6$" to --$R^6$--.

Claim 4, Column 19, Line 17, change "hydrogen halogen" to --hydrogen, halogen,--.

Signed and Sealed this

Twenty-sixth Day of December, 1995

Attest:

BRUCE LEHMAN

Attesting Officer

Commissioner of Patents and Trademarks